United States Patent
Nirogi et al.

(10) Patent No.: US 8,912,179 B2
(45) Date of Patent: Dec. 16, 2014

(54) HETEROCYCLYL COMPOUNDS AS HISTAMINE H₃ RECEPTOR LIGANDS

(75) Inventors: Ramakrishna Nirogi, Hyderabad (IN); Anil Karbhari Shinde, Hyderabad (IN); Ramasastri Kambhampati, Hyderabad (IN); Rambabu Namala, Hyderabad (IN); Adi Reddy Dwarampudi, Hyderabad (IN); Laxman Kota, Hyderabad (IN); Murlimohan Gampa, Hyderabad (IN); Padmavathi Kodru, Hyderabad (IN); Taraka Naga Vinaykumar Tiriveedhi, Hyderabad (IN); Vishwottam Nagaraj Kandikere, Hyderabad (IN); Nageshwara Rao Muddana, Hyderabad (IN); Ramanatha Shrikantha Saralaya, Hyderabad (IN); Pradeep Jayarajan, Hyderabad (IN); Dhanalakshmi Shanmuganathan, Hyderabad (IN); Ishtiyaque Ahmad, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 65 days.

(21) Appl. No.: 13/818,152

(22) PCT Filed: Nov. 15, 2010

(86) PCT No.: PCT/IN2010/000740
§ 371 (c)(1),
(2), (4) Date: Aug. 23, 2013

(87) PCT Pub. No.: WO2012/029070
PCT Pub. Date: Mar. 8, 2012

(65) Prior Publication Data
US 2014/0148440 A1 May 29, 2014

(30) Foreign Application Priority Data
Sep. 2, 2010 (IN) .......................... 2551/CHE/2010

(51) Int. Cl.
*A61K 31/535* (2006.01)
*A61K 31/55* (2006.01)
*C07D 513/04* (2006.01)
*C07D 413/12* (2006.01)
*C07D 417/12* (2006.01)
*C07D 471/04* (2006.01)
*C07D 498/04* (2006.01)

(52) U.S. Cl.
CPC ............ *C07D 513/04* (2013.01); *C07D 413/12* (2013.01); *C07D 417/12* (2013.01); *C07D 471/04* (2013.01); *C07D 498/04* (2013.01)
USPC ......... 514/234.2; 514/215; 514/301; 514/321

(58) Field of Classification Search
CPC .. C07D 413/12; C07D 417/12; C07D 471/04; C07D 498/04; C07D 513/04
USPC ................................ 514/215, 234.2, 301, 321
See application file for complete search history.

(56) References Cited

U.S. PATENT DOCUMENTS

| 4,695,575 A | 9/1987 | Janssens et al. |
| 8,394,842 B2 * | 3/2013 | Dorwald et al. ............... 514/367 |
| 2010/0292188 A1 * | 11/2010 | Denonne et al. ................ 514/81 |

FOREIGN PATENT DOCUMENTS

| EP | 0151826 A1 | 8/1985 | |
| WO | 03004480 A2 | 1/2003 | |
| WO | 2004022060 A2 | 3/2004 | |
| WO | WO 2006/008260 A1 | 1/2006 | |
| WO | WO 2008012010 A1 * | 1/2008 | ............ C07D 513/04 |
| WO | WO 2008/058096 A2 | 5/2008 | |
| WO | WO 2008/068173 A9 | 6/2008 | |
| WO | WO 2008/068174 A9 | 6/2008 | |
| WO | 2010026113 A1 | 3/2010 | |

OTHER PUBLICATIONS

A. U. Rao et al., "Synthesis and structure—activity relationships of 2-(1,40-bipiperidin-10-yl)thiazolopyridine as H3 receptor antagonists", 2009, Bioorg. Med. Chem. Lett., 19(21), pp. 6176-6180.*
Esbenshade et al., "The histamine H3 receptor: an attractive target for the treatment of cognitive disorders" British Journal of Pharmacology, 2008, 154(6), 1166-1181.

(Continued)

*Primary Examiner* — My-Chau T Tran
(74) *Attorney, Agent, or Firm* — McCarter & English, LLP; Steven G. Davis; Wei Song

(57) ABSTRACT

The present invention relates to heterocyclyl compounds of formula (I), and their pharmaceutically acceptable salts and compositions containing them. The present invention also relates to a process for the preparation of above said novel compounds, and their pharmaceutically acceptable salts. The compounds of formula (I) are useful in the treatment of various disorders that are related to Histamine H₃ receptors, for example cognitive disorders, sleep disorders, obesity and pain.

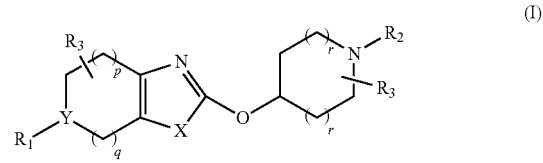

12 Claims, No Drawings

(56) References Cited

OTHER PUBLICATIONS

Passani et al., "The histamine H3 receptor as a novel therapeutic target for cognitive and sleep disorders" Trends in Pharmacology Science, 2004, 25(12), 618-625.

Esbenshade et al., "The histamine H3 receptor antagonists: preclinical promises for treating obesity and cognitive disorders" Molecular Interventions, 2006, 6(2), 77-88.

Medhurst et al., "Novel histamine H3 receptor antagonists GSK 185924 and GSK 334429 are efficacious in surgically-induced and virally-induced rat models of neuropathic pain" Pain, 2008, 138(1), 61-69.

Berge et al., "Pharmaceutical salts" Journal of Pharmaceutical Sciences, 1977, 66, 1-19.

International Search Report of PCT/IN2010/000740 mailed on Apr. 8, 2011.

Written Opinion of PCT/IN2010/000740 mailed on Apr. 8, 2011.

International Preliminary Report on Patentability of PCT/IN2010/000740 mailed on Aug. 31, 2012.

\* cited by examiner

HETEROCYCLYL COMPOUNDS AS HISTAMINE H₃ RECEPTOR LIGANDS

RELATED APPLICATIONS

This application is a 35 U.S.C. §371 national stage filing of International Application No. PCT/IN2010/000740, filed Nov. 15, 2010, which claims priority under 35 U.S.C. §365 to India Patent Application Serial No. 2551/CHE/2010, filed Sep. 2, 2010. The entire contents of each of the aforementioned applications are incorporated herein by reference in their entirety.

FIELD OF INVENTION

The present invention relates to heterocyclyl compounds of formula (I) and their pharmaceutically acceptable salts, its process of preparation and compositions containing them, for the treatment of various disorders that are related to Histamine $H_3$ receptors.

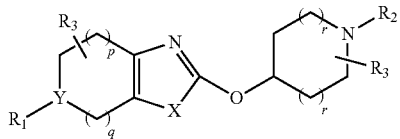

BACKGROUND OF THE INVENTION

Histamine H3 receptor is a G-protein coupled receptor (GPCR) and one out of the four receptors of Histamine family. Histamine H3 receptor is identified in 1983 and its cloning and characterization were done in 1999. Histamine $H_3$ receptor is expressed to a larger extent in central nervous system and lesser extent in the peripheral nervous system.

Literature evidence suggests that Histamine H3 receptors can be used in treatment of cognitive disorders (British Journal of Pharmacology, 2008, 154(6), 1166-1181), sleep disorders (Trends in Pharmacology Science, 2004, 25(12), 618-625), obesity (Molecular Interventions, 2006, 6 (2), 77-88) and pain (Pain, 2008, 138(1), 61-69).

Patents/Patent publications U.S. Pat. No. 4,695,575, EP0151826, WO2010026113, WO2004022060 and WO2003004480 disclosed series of compounds as ligands at Histamine H3 receptors. While some Histamine H3 receptor ligands have been disclosed, no compound till date is launched in market in this area of research, and there still exists a need and scope to discover new drugs with novel chemical structures for treatment of disorders affected by Histamine H3 receptors.

SUMMARY OF THE INVENTION

The present invention relates to novel Histamine $H_3$ receptor ligands of the formula (I);

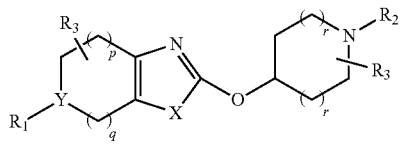

wherein,
$R_1$ is —C(O)—$R_4$, —S(O)$_2$—$R_4$,

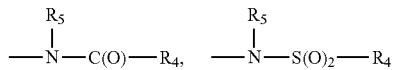
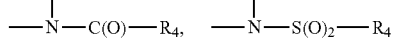

substituted or unsubstituted cycloalkyl, aryl or heteroaryl; wherein substituents, may be one or more and are independently selected from hydrogen, hydroxy, halogen, alkyl, alkoxy, haloalkyl or haloalkoxy;

$R_4$ is substituted or unsubstituted alkyl, cycloalkyl, cycloalkylalkyl, aryl, heteroaryl, heterocyclyl or heterocyclylalkyl; wherein substituents, may be one or more and are independently selected from hydrogen, hydroxy, halogen, alkyl, alkoxy, haloalkyl or haloalkoxy;

$R_5$ is hydrogen, alkyl or cycloalkyl;

at each occurrence, $R_3$ is independently selected from hydrogen, halo, alkyl or alkoxy;

$R_2$ is hydrogen, substituted or unsubstituted alkyl or cycloalkyl; wherein substituents, may be one or more and are independently selected from hydrogen, hydroxy, halogen, alkyl, alkoxy, haloalkyl or haloalkoxy;

X is S, N or O;
Y is C or N;
"p" is an integer ranging from 0 to 2;
"q" is an integer ranging from 0 to 2;
"r" is an integer ranging from 0 to 1; or a pharmaceutically acceptable salt thereof.

The present invention relates to use of a therapeutically effective amount of compound of formula (I), to manufacture a medicament in the treatment of various disorders that are related to Histamine H3 receptors.

Specifically, the compounds of this invention are useful in the treatment of various disorders such as cognitive disorders, sleep disorders, obesity and pain.

In another aspect, the invention relates to pharmaceutical compositions containing a therapeutically effective amount of at least one compound of formula (I), and pharmaceutically acceptable salts thereof, in admixture with pharmaceutical acceptable excipient.

In still another aspect, the invention relates to methods for using compounds of formula (I).

In yet another aspect, the invention further relates to the process for preparing compounds of formula (I) and their pharmaceutically acceptable salts.

Representative compounds of the present invention include those specified below and their pharmaceutically acceptable salts. The present invention should not be construed to be limited to them:

1-[2-(1-Cyclobutyl-piperidin-4-yloxy)-6,7-dihydro-4H-thiazolo[5,4-c]pyridin-5-yl]-propan-1-one tartrate;

[2-(4-Cyclobutyl-cyclohexyloxy)-4,5,7,8-tetrahydro-thiazolo[5,4-d]azepin-6-yl]-cyclopropyl-methanone tartrate;

N-[2-(1-Cyclobutyl-piperidin-4-yloxy)-4,5,6,7-tetrahydro-benzothiazol-6-yl]-propionamide;

[2-(1-Cyclobutyl-piperidin-4-yloxy)-6,7-dihydro-4H-thiazolo[5,4-c]pyridin-5-yl]-cyclopropyl-methanone tartrate;
Cyclobutyl-[2-(1-cyclobutyl-piperidin-4-yloxy)-6,7-dihydro-4H-thiazolo[5,4-c]pyridin-5-yl]-methanone tartrate;
[2-(1-Cyclobutyl-piperidin-4-yloxy)-6,7-dihydro-4H-thiazolo[5,4-c]pyridin-5-yl]-(2-fluoro-phenyl)-methanone tartrate;
1-[2-(1-Cyclobutyl-piperidin-4-yloxy)-6,7-dihydro-4H-thiazolo[5,4-c]pyridin-5-yl]-3-methyl-butan-1-one tartrate;
Cyclobutyl-[2-(1-isopropyl-piperidin-4-yloxy)-6,7-dihydro-4H-thiazolo[5,4-c]pyridin-5-yl]-methanone;
Cyclopropyl-[2-(1-isopropyl-piperidin-4-yloxy)-6,7-dihydro-4H-thiazolo[5,4-c]pyridin-5-yl]-methanone tartrate;
Cyclopropyl-[2-(1-cyclopropyl-piperidin-4-yloxy)-6,7-dihydro-4H-thiazolo[5,4-c]pyridin-5-yl]-methanone tartrate;
Cyclobutyl-[2-(1-cyclopropyl-piperidin-4-yloxy)-6,7-dihydro-4H-thiazolo[5,4-c]pyridin-5-yl]-methanone tartrate;
1-[2-(1-Cyclobutyl-piperidin-4-yloxy)-6,7-dihydro-4H-thiazolo[5,4-c]pyridin-5-yl]-2-morpholin-4-yl-ethanone tartrate;
[4-(5-Cyclobutyl-6,7-dihydro-4H-thiazolo[5,4-c]pyridin-2-yloxy)-piperidin-1-yl]-cyclopropyl-methanone tartrate;
[3-(5-Cyclobutyl-6,7-dihydro-4H-thiazolo[5,4-c]pyridin-2-yloxy)-piperidin-1-yl]-cyclopropyl-methanone tartrate;
[2-(1-Cyclobutyl-piperidin-3-yloxy)-6,7-dihydro-4H-thiazolo[5,4-c]pyridin-5-yl]-cyclopropyl-methanone tartrate;
[2-(1-Cyclobutyl-piperidin-4-yloxy)-6,7-dihydro-4H-thiazolo[5,4-c]pyridin-5-yl]-pyridin-4-yl-methanone tartrate;
[2-(1-Cyclobutyl-piperidin-4-yloxy)-6,7-dihydro-4H-thiazolo[5,4-c]pyridin-5-yl]-(4-methoxy-phenyl)-methanone tartrate;
1-[2-(1-Cyclobutyl-piperidin-4-yloxy)-6,7-dihydro-4H-thiazolo[5,4-c]pyridin-5-yl]-2-piperidin-1-yl-ethanone tartrate;
1-[2-(1-Cyclobutyl-piperidin-4-yloxy)-6,7-dihydro-4H-thiazolo[5,4-c]pyridin-5-yl]-2-cyclopropyl-ethanone;
2-(1-Cyclobutyl-piperidin-4-yloxy)-5-(2-fluoro-benzenesulfonyl)-6,7-dihydro-4H-thiazolo[5,4-c]pyridine tartrate;
2-(1-Cyclobutyl-piperidin-4-yloxy)-5-methanesulfonyl-6,7-dihydro-4H-thiazolo[5,4-c]pyridine;
1-[2-(1-Cyclobutyl-piperidin-4-yloxy)-6,7-dihydro-4H-thiazolo[5,4-c]pyridin-5-yl]-2-methyl-propan-1-one tartrate;
2-(1-Cyclobutyl-piperidin-4-yloxy)-5-(2-trifluoromethyl-pyridin-5-yl)-6,7-dihydro-4H-thiazolo[5,4-c]pyridine;
Cyclopropyl-[2-(1-isobutyl-piperidin-4-yloxy)-6,7-dihydro-4H-thiazolo[5,4-c]pyridin-5-yl]-methanone tartrate;
[2-(1-Cyclobutyl-piperidin-4-yloxy)-6,7-dihydro-4H-thiazolo[5,4-c]pyridin-5-yl]-(2-trifluoromethyl-pyridin-5-yl)-methanone;
[2-(1-Cyclobutyl-piperidin-4-yloxy)-6,7-dihydro-4H-thiazolo[5,4-c]pyridin-5-yl]-pyridin-3-yl-methanone tartrate;
2-(1-Cyclobutyl-piperidin-4-yloxy)-5-pyridin-3-yl-6,7-dihydro-4H-thiazolo[5,4-c]pyridine tartrate;
[2-(1-Cyclobutyl-piperidin-4-yloxy)-6,7-dihydro-4H-thiazolo[5,4-c]pyridin-5-yl]-(tetrahydro-pyran-4-yl)-methanone;
[2-(1-Cyclobutyl-piperidin-4-yloxy)-6,7-dihydro-4H-thiazolo[5,4-c]pyridin-5-yl]-morpholin-4-yl-methanone tartrate;
[2-(1-Cyclobutyl-piperidin-4-yloxy)-6,7-dihydro-4H-thiazolo[5,4-c]pyridin-5-yl]-piperidin-1-yl-methanone hydrochloride;
6-[2-(1-Cyclobutyl-piperidin-4-yloxy)-6,7-dihydro-4H-thiazolo[5,4-c]pyridin-5-yl]-nicotinamide;
[2-(1-Cyclobutyl-piperidin-4-yloxy)-6,7-dihydro-4H-thiazolo[5,4-c]pyridin-5-yl]-cyclopentyl-methanone tartrate;
[2-(1-Cyclobutyl-piperidin-4-yloxy)-6,7-dihydro-5H-thiazolo[5,4-b]pyridin-4-yl]-cyclopropyl-methanone tartrate;
Cyclopropyl-[2-(1-isopropyl-piperidin-4-yloxy)-4,5,7,8-tetrahydro-thiazolo[5,4-d]azepin-6-yl]-methanone tartrate;
[2-(1-Cyclobutyl-piperidin-4-yloxy)-6,7-dihydro-5H-thiazolo[5,4-b]pyridin-4-yl]-cyclopropyl-methanone;
1-[2-(1-Cyclobutyl-piperidin-4-yloxy)-6,7-dihydro-5H-thiazolo[5,4-b]pyridin-4-yl]-propan-1-one;
Cyclobutyl-[2-(1-cyclobutyl-piperidin-4-yloxy)-6,7-dihydro-5H-thiazolo[5,4-b]pyridin-4-yl]-methanone;
N-[2-(1-Cyclobutyl-piperidin-4-yloxy)-4,5,6,7-tetrahydro-benzothiazol-7-yl]-propionamide;
1-[2-(1-Cyclobutyl-piperidin-4-yloxy)-6,7-dihydro-4H-oxazolo[5,4-c]pyridin-5-yl]-propan-1-one;
1-[2-(1-Cyclobutyl-piperidin-4-yloxy)-4,6-dihydro-pyrrolo[4,3-d]oxazol-5-yl]-propan-1-one;
N-[2-(1-Cyclobutyl-piperidin-4-yloxy)-5,6-dihydro-4H-cyclopentaoxazol-5-yl]-propionamide;
N-[2-(1-Cyclobutyl-piperidin-4-yloxy)-5,6-dihydro-4H-cyclopentathiazol-5-yl]-propionamide;
1-[2-(1-Cyclobutyl-piperidin-4-yloxy)-4,6-dihydro-pyrrolo[4,3-d]thiazol-5-yl]-propan-1-one;
1-[2-(1-Cyclobutyl-piperidin-4-yloxy)-5,6-dihydro-pyrrolo[3,2-d]thiazol-4-yl]-propan-1-one;
N-[2-(1-Cyclobutyl-piperidin-4-yloxy)-5,6-dihydro-4H-cyclopentathiazol-6-yl]-propionamide;
N-[2-(1-Cyclobutyl-piperidin-4-yloxy)-5,6-dihydro-4H-cyclopentaoxazol-6-yl]-propionamide;
1-[2-(1-Cyclobutyl-piperidin-4-yloxy)-5,6-dihydro-pyrrolo[3,2-d]oxazol-4-yl]]-propan-1-one;
1-[2-(1-Cyclobutyl-piperidin-4-yloxy)-4,6-dihydro-pyrrolo[4,3-d]oxazol-5-yl]-propan-1-one;
N-[2-(1-Cyclobutyl-piperidin-4-yloxy)-5,6-dihydro-4H-cyclopentaoxazol-5-yl]-propionamide;
1-[2-(1-Cyclobutyl-piperidin-4-yloxy)-4,6,7,8-tetrahydro-thiazolo[5,4-c]azepin-5-yl]-propan-1-one;
1-[2-(1-Cyclobutyl-piperidin-4-yloxy)-4-methyl-6,7-dihydro-4H-thiazolo[5,4-c]pyridin-5-yl]-propan-1-one;
1-[2-(1-Cyclobutyl-piperidin-4-yloxy)-7-fluoro-6,7-dihydro-4H-thiazolo[5,4-c]pyridin-5-yl]-propan-1-one;
1-[2-(1-Cyclobutyl-piperidin-4-yloxy)-7-methyl-6,7-dihydro-4H-thiazolo[5,4-c]pyridin-5-yl]-propan-1-one;
1-[2-(1-Cyclobutyl-piperidin-4-yloxy)-6-methyl-6,7-dihydro-4H-thiazolo[5,4-c]pyridin-5-yl]-propan-1-one;
1-[2-(1-Cyclobutyl-3-methyl-piperidin-4-yloxy)-6,7-dihydro-4H-thiazolo[5,4-c]pyridin-5-yl]-propan-1-one;
1-[2-(1-Cyclobutyl-3-fluoro-piperidin-4-yloxy)-6,7-dihydro-4H-thiazolo[5,4-c]pyridin-5-yl]-propan-1-one;
1-Cyclobutyl-4-(5-propionyl-4,5,6,7-tetrahydro-thiazolo[5,4-c]pyridin-2-yloxy)-piperidine-3-carbonitrile;
1-[2-(1-Cyclobutyl-azepan-4-yloxy)-6,7-dihydro-4H-thiazolo[5,4-c]pyridin-5-yl]-propan-1-one;
1-[2-(1-Cyclobutyl-azepan-4-yloxy)-4,5,7,8-tetrahydro-thiazolo[5,4-d]azepin-6-yl]-propan-1-one;
1-[2-(1-Cyclobutyl-pyrrolidin-3-yloxy)-4,5,7,8-tetrahydro-thiazolo[5,4-d]azepin-6-yl]-propan-1-one;
1-[2-(1-Cyclobutyl-pyrrolidin-3-yloxy)-4,6-dihydro-pyrrolo[4,3-d]thiazol-5-yl]-propan-1-one;
1-[2-(1-Cyclobutyl-azepan-4-yloxy)-4,6-dihydro-pyrrolo[4,3-d]thiazol-5-yl]-propan-1-one;
1-{2-[1-(2-Hydroxy-ethyl)-piperidin-4-yloxy]-6,7-dihydro-4H-thiazolo[5,4-c]pyridin-5-yl}-propan-1-one;
1-[2-(1-Ethoxymethyl-piperidin-4-yloxy)-6,7-dihydro-4H-thiazolo[5,4-c]pyridin-5-yl]-propan-1-one;

1-{2-[1-(2,2,2-Trifluoro-ethyl)-piperidin-4-yloxy]-6,7-dihydro-4H-thiazolo[5,4-c]pyridin-5-yl}-propan-1-one;

1-[2-(1-Cyclobutyl-azetidin-3-yloxy)-6,7-dihydro-4H-thiazolo[5,4-c]pyridin-5-yl]-propan-1-one; and their pharmaceutically acceptable salts.

DETAILED DESCRIPTION OF THE INVENTION

Unless otherwise stated, the following terms used in the specification and claims have the meanings given below:

The term "halogen" means fluorine, chlorine, bromine or iodine.

The term "alkyl" means straight chain or branched hydrocarbon radical consisting solely of carbon and hydrogen atoms, containing no unsaturation, having from one to eight carbon atoms, and which is attached to the rest of the molecule by a single bond. Exemplary "alkyl" groups include methyl, ethyl, n-propyl, iso-propyl and the like.

The term "alkoxy" means an alkyl group attached via an oxygen linkage to the rest of the molecule. Exemplary "alkoxy" groups include methoxy, ethoxy, propyloxy, iso-propyloxy and the like.

The term "haloalkyl" means straight or branched chain alkyl radicals containing one to three carbon atoms. Exemplary "haloalkyl" groups include fluoromethyl, difluoromethyl, trifluoromethyl, trifluoroethyl, fluoroethyl, difluoroethyl and the like.

The term "haloalkoxy" means straight or branched chain alkoxy radicals containing one to three carbon atoms. Exemplary "haloalkoxy" groups include fluoromethoxy, difluoromethoxy, trifluoromethoxy, trifluoroethoxy, fluoroethoxy, difluoroethoxy and the like.

The term "cycloalkyl" means non-aromatic mono cyclic ring of 3 to 8 carbon atoms. Exemplary "cycloalkyl" groups include cyclopropyl, cyclobutyl, cyclopentyl and the like.

The term "cycloalkylalkyl" means cycloalkyl ring radical directly bonded to an alkyl group.

The term "aryl" means any functional group or substituent derived from a simple aromatic ring, Exemplary "aryl" groups include phenyl, naphthyl and the like.

The term "heteroaryl" means organic compounds that contain a ring structure containing atoms in addition to carbon such as sulfur, oxygen or nitrogen, as part of the ring, these additional atoms may be repeated more than once in ring. These rings may be either simple aromatic rings. Exemplary "heteroaryl" groups include pyridine, pyrimidine, benzofuranyl, benzothiophene, furyl, dioxalanyl, pyrrolyl, oxazolyl, pyridyl, pyridazinyl, pyrimidinyl, pyrazinyl, quinolinyl, indolyl and the like.

The term "heterocyclyl" means non-aromatic mono cyclic ring of 2 to 7 carbon atoms, whose ring structures include 1 to 3 heteroatoms, these additional atoms may be repeated more than once in ring. Exemplary "heterocyclyl" groups include pyrrolidinyl, piperidinyl, piperazinyl, morpholinyl and the like.

The term "heterocyclylalkyl" means heterocyclyl ring radical directly bonded to an alkyl group.

The terms "treating", "treat" or "treatment" embrace all the meanings such as preventative, prophylactic and palliative.

The phrase "pharmaceutically acceptable salts" indicates that the substance or composition must be compatible chemically and/or toxicologically, with the other ingredients comprising a formulation, the mammal being treated therewith.

The phrase "therapeutically effective amount" is defined as 'an amount of a compound of the present invention that (i) treats or prevents the particular disease, condition or disorder (ii) attenuates, ameliorates or eliminates one or more symptoms of the particular disease, condition or disorder (iii) prevents or delays the onset of one or more symptoms of the particular disease, condition or disorder described herein.

Commercial reagents were utilized without further purification. Room temperature refers to 25-40° C. Unless otherwise stated, all mass spectra were carried out using ESI conditions. $^1$H-NMR spectra were recorded at 400 MHz on a Bruker instrument. Deuterated chloroform (99.8% D), methanol or dimethylsulfoxide was used as solvent. TMS was used as internal reference standard. Chemical shift values are expressed in parts per million (δ) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

The compounds nomenclature is generated by using Chem Draw Ultra 7.0.

Pharmaceutical Compositions

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable excipient. The pharmaceutically acceptable excipient is carrier or diluent. Thus, the active compounds of the invention may be formulated for oral, intranasal or parenteral (e.g., intravenous, intramuscular or subcutaneous). Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors.

Method of Preparation

The compounds of formula (I) can be prepared by Scheme I as shown below.

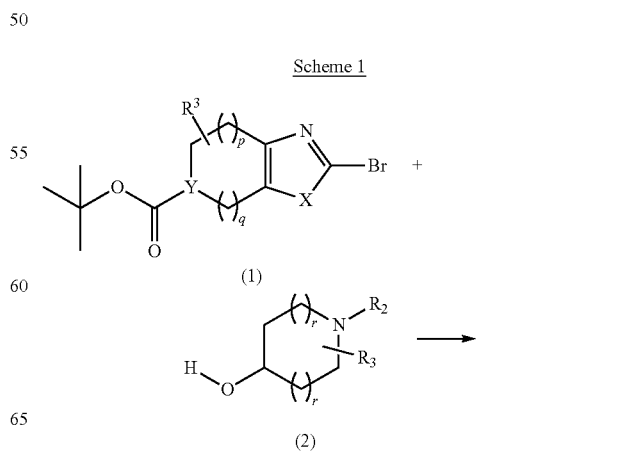

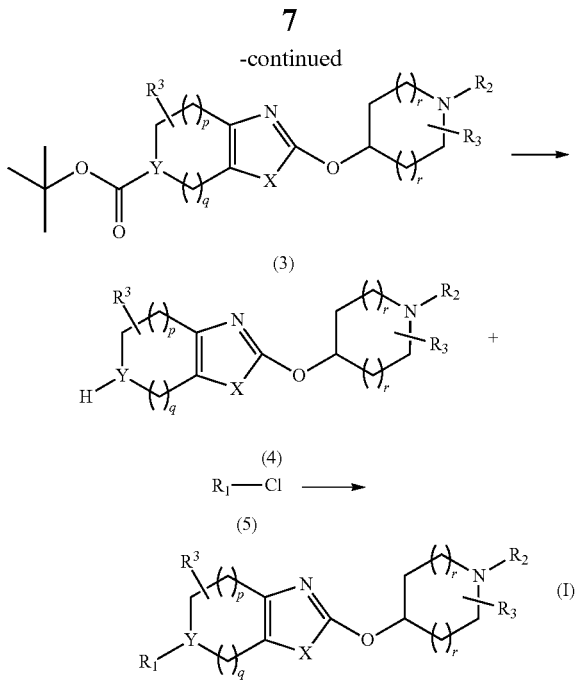

In above Scheme I, p is 1; q is 1; r is 1; Y is N; X is S; R$_1$ is —C(O)—R$_4$, —S(O)$_2$—R$_4$, substituted or unsubstituted cycloalkyl, aryl or heteroaryl, and all other symbols are as defined above.

The compound of formula (1) is coupled with compound of formula (2) to form compound of formula (3). The compound of formula (3) is deprotected to form compound of formula (4). The compound of formula (4) is coupled with compound of formula (5) to form compound of formula (I).

In the first step of the above preparation, the compound of formula (1) is coupled with compound of formula (2) to form compound formula (3). This reaction is preferably carried out in solvent such as tetrahydrofuran, toluene, ethyl acetate, dichloromethane, triethylamine, dimethylformamide, and the like or a mixture thereof and preferably by using tetrahydrofuran. The reaction may be affected in the presence of a base such as sodium hydride, sodium carbonate, potassium carbonate, sodium bicarbonate, sodium hydroxide or mixtures thereof and preferably by using sodium hydride. The reaction is carried out at room temperature. The duration of the reaction may range from 4 to 8 hours, preferably from a period of 5 to 7 hours.

In the second step of the above preparation, the compound of formula (3) is deprotected to form compound of formula (4). This reaction is preferably carried out in solvent such as tetrahydrofuran, toluene, ethyl acetate, dichloromethane, acetonitrile, 1,4-dioxone, dimethylformamide, and the like or a mixture thereof and preferably by using dichloromethane. The reaction may be affected in the presence of a acid such as trifluoroacetic acid, sulfuric acid, acetic acid, perchloric acid, hydrochloric acid, and the like or a mixture thereof and preferable by using trifluoroacetic acid. The reaction is carried out at temperature of 60° C. to 85° C. and preferably temperature in range of 65° C. to 75° C. The duration of the reaction may range from 2 to 6 hours, preferably from a period of 3 to 5 hours.

In the third step of the above preparation, the compound of formula (4) is coupled with compound of formula (5) to form compound of formula (I). This reaction is preferably carried out in solvent such as dichloromethane, tetrahydrofuran, toluene, ethyl acetate, dimethylformamide, and the like or a mixture thereof and preferably by using dichloromethane. The reaction may be affected in the presence of a base such as triethylamine, potassium carbonate, diisopropylethylamine and pyridine and preferable by using triethylamine. The reaction is carried out at room temperature. The duration of the reaction may range from 15 minutes to 45 minutes, preferably from a period of 25 minutes to 35 minutes.

The compounds of formula (1), formula (2) and formula (5) may be commercially available or can be prepared by conventional methods or by modification, using known process.

The compounds of formula (I) can also be prepared by using Scheme II as shown below Scheme II

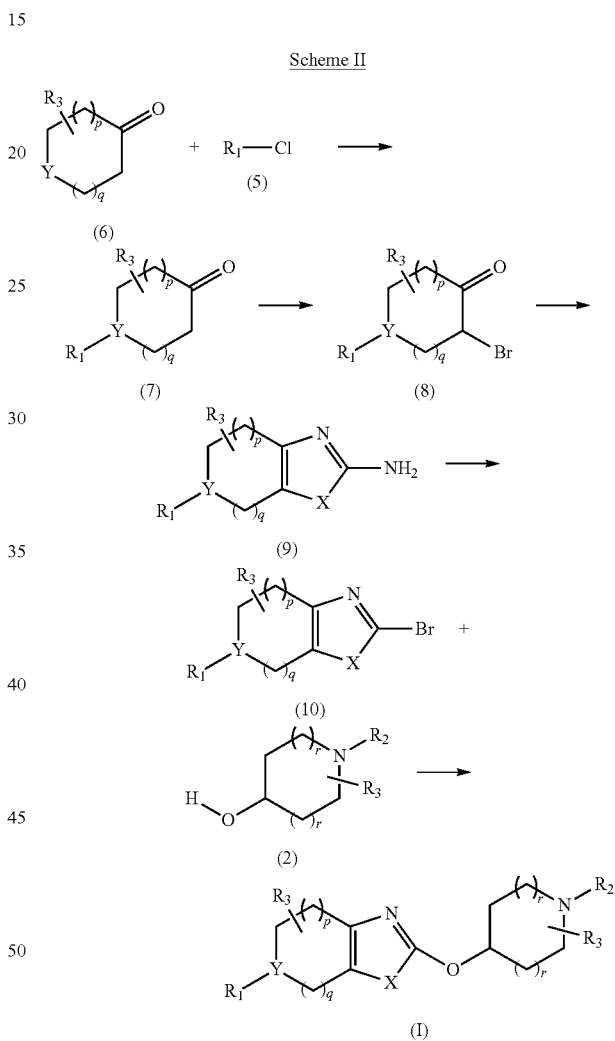

In above Scheme II, p is 1; q is 2; r is 1; Y is N; X is S; R$_1$ is —C(O)—R$_4$, —S(O)$_2$—R$_4$, substituted or unsubstituted cycloalkyl, aryl or heteroaryl, and all other symbols are as defined above.

The compound of formula (6) is coupled with compound of formula (5) to form compound of formula (7). The compound of formula (7) is brominated to form compound of formula (8). The compound of formula (8) is cyclized to form compound of formula (9). The compound of formula (9) is diazotized to form compound of formula (10). The compound of formula (10) is coupled with compound of formula (2) to form compound of formula (I).

In the first step of the above preparation, the compound of formula (6) is coupled with compound of formula (5) to form compound of formula (7). This reaction is preferably carried out in solvent such as tetrahydrofuran, toluene, ethyl acetate, dichloromethane, dimethylformamide, and the like or a mixture thereof and preferably by using dichloromethane. The reaction may be affected in the presence of a base such as triethylamine, potassium carbonate, diisopropylethylamine and pyridine and preferable by using triethylamine. The reaction is carried out at room temperature. The duration of the reaction may range from 15 minutes to 45 minutes, preferably from a period of 25 minutes to 35 minutes.

In the second step of the above preparation, the compound of formula (7) is brominated to form compound of formula (8). The reaction may be affected in the presence of an acid such as sulfuric acid, acetic acid, perchloric acid, hydrochloric acid, and the like or a mixture thereof and preferable by using acetic acid. The reaction may be affected in the presence of a bromating agent such as bromine, copper (II) bromide, hydrobromic acid, N-bromosuccinimide, pyridine hydrobromide perbromide, tetrabromomethane, and the like or a mixture thereof and preferably by using bromine. The reaction is carried out at room temperature. The duration of the reaction may range from 16 hours to 20 hours preferably from a period of 17 hours to 19 hours.

In the third step of the above preparation, the compound of formula (8) is cyclized to form compound of formula (9). This reaction is preferably carried out in solvent such as isopropyl alcohol, tetrahydrofuran, toluene, ethyl acetate, dichloromethane, triethylamine, dimethylformamide, and the like or a mixture thereof and preferably by using isopropyl alcohol. The reaction may be affected in the presence of urea or thiourea. The reaction is carried out at temperature of 60° C. to 85° C. and preferably temperature in range of 65° C. to 75° C. The duration of the reaction may range from 15 minutes to 45 minutes, preferably from a period of 25 minutes to 35 minutes.

In the fourth step of the above preparation, the compound of formula (9) is diazotized to form compound of formula (10). This reaction is preferably carried out in solvent such as acetonitrile, tetrahydrofuran, isopropyl alcohol, toluene, ethyl acetate, dichloromethane, triethylamine, dimethylformamide, and the like or a mixture thereof and preferably by using acetonitrile. The reaction may be affected in the presence of a brominating agent such as copper (II) bromide, hydrobromic acid, N-bromosuccinimide, pyridine hydrobromide perbromide, tetrabromomethane, and the like or a mixture thereof and preferably by using copper (II) bromide. The reaction may be affected in the presence of alkyl nitrites and preferably by using tert-butyl nitrite. The reaction is carried out at room temperature. The duration of the reaction may range from 15 minutes to 45 minutes, preferably from a period of 25 minutes to 35 minutes.

In the fifth step of the above preparation, the compound of formula (10) is coupled with compound of formula (2) to form compound of formula (I). This reaction is preferably carried out in solvent such as tetrahydrofuran, toluene, ethyl acetate, dichloromethane, triethylamine, dimethylformamide, and the like or a mixture thereof and preferably by using tetrahydrofuran. The reaction may be affected in the presence of a base such as sodium hydride, sodium carbonate, potassium carbonate, sodium bicarbonate, sodium hydroxide, or mixtures thereof and preferably by using sodium hydride. The reaction may be affected in the presence of urea or thiourea. The reaction is carried out at temperature of 60° C. to 85° C. and preferably temperature in range of 65° C. to 75° C. The duration of the reaction may range from 12 to 18 hours, preferably from a period of 14 to 16 hours.

The compounds of formula (2), formula (5) and formula (6) may be commercially available or can be prepared by conventional methods or by modification, using known process.

The compounds of formula (I) can also be prepared by using Scheme III as shown below

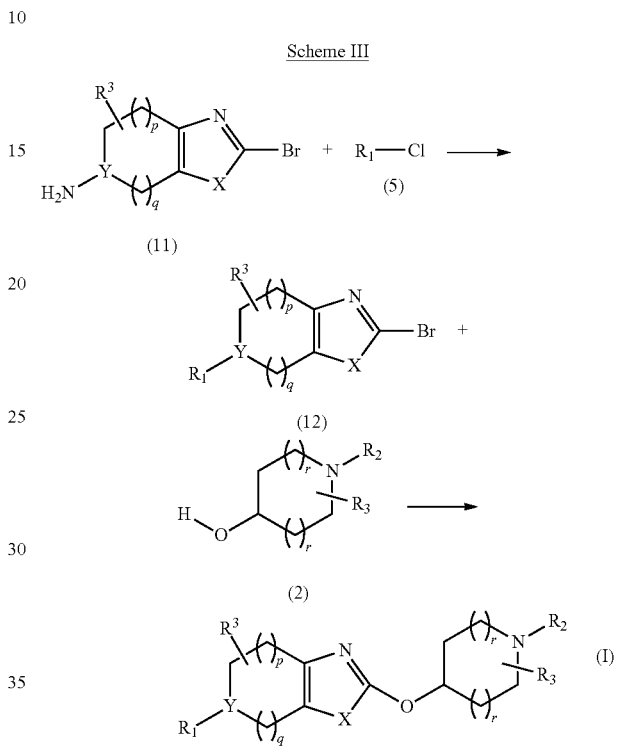

In above Scheme III, p is 1; q is 1; r is 1; Y is C; X is S; $R_1$ is

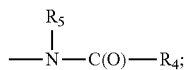

and all other symbols are as defined above.

The compound of formula (11) is coupled with compound of formula (5) to form compound of formula (12). The compound of formula (12) is coupled with compound of formula (2) to form compound of formula (I).

In the first step of the above preparation, the compound of formula (11) is coupled with compound of formula (5) to form compound of formula (12). This reaction is preferably carried out in solvent such as tetrahydrofuran, toluene, ethyl acetate, dichloromethane, dimethylformamide, and the like or a mixture thereof and preferably by using dicloromethane. The reaction may be affected in the presence of a base such as triethylamine, potassium carbonate, diisopropylethylamine and pyridine and preferable by using triethylamine. The reaction is carried out at room temperature. The duration of the reaction may range from 15 minutes to 45 minutes, preferably from a period of 25 minutes to 35 minutes.

In the second step of the above preparation, the compound of formula (12) is coupled with compound of formula (2) to form compound formula (I). This reaction is preferably carried out in solvent such as tetrahydrofuran, toluene, ethyl acetate, dichloromethane, triethylamine, dimethylformamide, and the like or a mixture thereof and preferably by using dimethylformamide. The reaction may be affected in the presence of a base such as sodium hydride, sodium carbonate, potassium carbonate, sodium bicarbonate, sodium hydroxide or mixtures thereof and preferably by using sodium hydride. The reaction is carried out at room temperature. The duration of the reaction may range from 45 to 51 hours, preferably from a period of 47 to 49 hours.

The compounds of formula (2), formula (5) and formula (11) may be commercially available or can be prepared by conventional methods or by modification, using known process.

If necessary, any one or more than one of the following steps can be carried out,
i) converting a compound of the formula (I) into another compound of the formula (I) or
ii) forming a pharmaceutically acceptable salt.

Process (i) may be performed by further chemical modifications using well known reactions such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.

In process (ii) pharmaceutically acceptable salts may be prepared conventionally by reaction with the appropriate acid or acid derivative.

Suitable pharmaceutically acceptable salts will be apparent to those skilled in the art and include those described in J. Pharm. Sci., 1977, 66, 1-19, such as acid addition salts formed with inorganic acids e. g. hydrochloric, hydrobromic, sulfuric, nitric or phosphoric acid and organic acids e. g. succinic, maleic, acetic, fumaric, citric, malic, tartaric, benzoic, p-toluic, p-toluenesulfonic, methanesulfonic or naphthalenesulfonic acid.

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used.

EXAMPLES

The novel compounds of the present invention were prepared according to the following experimental procedures, using appropriate materials and appropriate conditions.

Preparation 1

Preparation of 2-Bromo-6,7-dihydro-4H-thiazolo[5,4-c]pyridine-5-carboxylic acid tert-butyl ester Step (i): Preparation of 3-Bromo-4-oxo-piperidine-1-carboxylic acid tert-butyl ester A solution of 4-Oxo-piperidin-1-carboxylic acid tert-butyl ester (10 grams, 50 mmol) and aluminium chloride (0.67 grams, 5 mmol) in tetrahydrofuran (30 mL) and diethyl ether (30 mL) was cooled to 0° C., and then treated with bromine (2.6 mL, 50 mmol) over a period of 30 minutes. Stirred the reaction mass for 24 hours at 0-5° C. After completion of reaction, the obtain solids were filtered and the mother liquor was concentrated under vacuum. The obtain crude was triturated with diethyl ether and solids were filtered and dried under vacuum to obtain the title compound (10 grams).

$^1$H-NMR (δ ppm): 1.51 (9H, s), 2.42-2.48 (1H, m), 3.04 (1H, m), 3.59-3.74 (2H, m), 3.97 (2H, m), 4.33 (1H, m);
Mass (m/z): 278 (M+H)$^+$, 280 (M+3H)$^+$.

Step (ii): Preparation of 2-Amino-6,7-dihydro-4H-thiazolo[5,4-c]pyridine-5-carboxylic acid tert-butyl ester A suspension of 3-Bromo-4-oxo-piperidine-1-carboxylic acid tert-butyl ester (10 grams, 35 mmol, obtained in above step) and thiourea (3.28 grams, 42 mmol) in isopropanol (100 mL) was refluxed for 1 hour. After completion of reaction, reaction mass was concentrated and resulted crude was triturated with diethyl ether (50 mL), solids were filtered and dried under vacuum to obtain the title compound (10 grams).

$^1$H-NMR (δ ppm): 1.39 (9H, s), 2.52 (2H, m), 3.56-3.59 (2H, t), 4.30 (2H, s), 7.10 (2H, bs);
Mass (m/z): 256 (M+H)$^+$.

Step (iii): Preparation of 2-Bromo-6,7-dihydro-4H-thiazolo[5,4-c]pyridine-5-carboxylic acid tert-butyl ester A solution of 2-Amino-6,7-dihydro-4H-thiazolo[5,4-c]pyridine-5-carboxylic acid tert-butyl ester (10 grams, 40 mmol, obtained in above step) and copper (II) bromide (9.6 grams, 43 mmol) in acetonitrile (50 mL) was cooled to 0° C. Tert-butyl nitrite (5.1 mL, 43 mmol) was added drop wise over a period of 30 minutes at 0° C. Stirred the reaction mass for 30 minutes and the reaction mass was quenched with 6N hydrochloric acid solution. Product was extracted with ethyl acetate (3×100 mL), combined organics were washed with water followed by brine and dried over anhydrous sodium sulphate. Organic volatiles were evaporated under vacuum. The residue obtained was purified by flash chromatography (ethyl acetate/n-hexane, 0.5/9.5) to obtain the title compound (3.0 grams).

$^1$H-NMR (δ ppm): 1.49 (9H, s), 2.85 (2H, m), 3.72 (2H, m), 4.56 (2H, s);
Mass (m/z): 319.3 (M+H)$^+$, 321.3 (M+H)$^+$.

Preparation 2

Preparation of (2-Bromo-4,5,6,7-tetrahydro-benzothiazol-6-yl)-carbamic acid tert-butyl ester Step (i): Preparation of (3-Bromo-4-oxo-cyclohexyl)-carbamic acid tert-butyl ester A solution of (4-Oxo-cyclohexyl)-carbamic acid tert-butyl ester (10 grams, 46 mmol) and aluminum chloride (0.25 grams, 2 mmol) in tetrahydrofuran (30 mL) and diethyl ether (30 mL) was cooled to 0° C., then treated with bromine (2.4 mL, 46 mmol) over a period of 30 minutes. The reaction mass was stirred for 24 hours at 0-5° C. After completion of reaction, the obtained solids were filtered and lower filtrate was concentrated under vacuum. The obtained crude was triturated with diethyl ether and the resulted solids were filtered and dried under vacuum to obtain the title compound (9.0 grams).

Mass (m/z): 292.3 (M+H)$^+$, 294.3 (M+3H)$^+$.

Step (ii): Preparation of 2-Amino-4,5,6,7-tetrahydro-benzothiazol-6-yl)-carbamic acid tert-butyl ester A suspension of 3-Bromo-4-oxo-piperidine-1-carboxylic acid tert-butyl ester (9 grams, 31 mmol, obtained in above step) and thiourea (2.4 grams, 31 mmol) in isopropanol (100 mL) was refluxed for 1 hour. After completion of reaction, reaction mass was concentrated and resulted crude was triturated with diethyl ether (50 mL), solids were filtered and dried under vacuum to obtain the title compound (9 grams).

$^1$H-NMR (δ ppm): 1.38 (9H, s), 1.61-1.71 (1H, m), 1.84-1.86 (1H, m), 2.29-2.35 (1H, m), 2.53-2.57 (2H, m), 2.71-2.76 (1H, m), 3.71-3.76 (1H, m), 9.11 (2H, s), 12.86-12.93 (1H, bs);

Mass (m/z): 270.3 $(M+H)^+$.

Step (iii): Preparation of (2-Bromo-4,5,6,7-tetrahydro-benzothiazol-6-yl)-carbamic acid tert-butyl ester A solution of 2-Amino-4,5,6,7-tetrahydro-benzothiazol-6-yl)-carbamic acid tert-butyl ester (9 grams, 33 mmol, obtained in above step) and copper (II) bromide (8.3 grams, 37 mmol) in acetonitrile (70 mL) was cooled to 0° C. The resulting mass was treated with tert-butyl nitrite (4.5 mL, 37 mmol) over a period of 30 minutes at 0° C. The reaction mass was stirred for 30 minutes and quenched with 6N hydrochloric acid solution. Product was extracted with ethyl acetate (3×100 mL), combined organics were washed with water followed by brine and dried over anhydrous sodium sulphate. Organic volatiles were evaporated under vacuum. The residue was purified by flash chromatography (ethylacetate/n-hexane, 0.5/9.5) to obtain the title compound (2.3 grams).

$^1$H-NMR (δ ppm): 1.45 (9H, s), 1.89-1.93 (1H, m), 2.03-2.07 (1H, m), 2.59-2.63 (1H, m), 2.85-2.91 (1H, m), 3.09-3.13 (1H, m), 4.05-4.09 (1H, m), 4.63-4.66 (1H, m), 12.36-12.42 (1H, bs);

Mass (m/z): 333.1 $(M+H)^+$, 335.3 $(M+3H)^+$.

Example 1

Preparation of 1-[2-(1-Cyclobutyl-piperidin-4-yloxy)-6,7-dihydro-4H-thiazolo[5,4-c]pyridin-5-yl]-propan-1-one tartrate

Step (i): Preparation of 2-(1-Cyclobutyl-piperidin-4-yloxy)-6,7-dihydro-4H-thiazolo[5,4-c]pyridine-5-carboxylic acid tert-butyl ester 1-Cyclobutyl-piperidin-4-ol (1.6 grams, 10 mmol) in tetrahydrofuran (20 mL) was treated with cooled and stirred suspension of sodium hydride (0.9 grams, 18 mmol) in tetrahydrofuran (20 mL) slowly over a period of 30 minutes; the reaction mixture was stirred for 1 hour. A solution of 2-Bromo-6,7-dihydro-4H-thiazolo[5,4-c]pyridine-5-carboxylic acid tert-butyl ester (3 grams, 9 mmol, obtained in preparation 1) in tetrahydrofuran (30 mL) was added drop wise over a period of 15 minutes and refluxed the reaction for 6 hours. Reaction mass was quenched with ice cold water and the product was extracted with ethyl acetate (3×50 mL). Combined organics were washed with water followed by brine and dried over anhydrous sodium sulphate. Organic volatiles were evaporated under vacuum. The residue was purified by flash chromatography (ethylacetate/n-hexane, 1/1) to obtain the title compound (2.0 grams).

$^1$H-NMR (δ ppm): 1.48 (9H, s), 1.65-1.72 (2H, m), 1.85-1.92 (4H, m), 2.01-2.07 (4H, m), 2.18-2.19 (2H, m), 2.57 (2H, m), 2.62-2.66 (2H, m), 2.71-2.75 (1H, m), 3.70 (2H, m), 4.43 (2H, m), 4.93 (1H, m);

Mass (m/z): 394.2 $(M+H)^+$.

Step (ii): Preparation of 2-(1-Cyclobutyl-piperidin-4-yloxy)-4,5,6,7-tetrahydro-thiazolo[5,4-c]pyridine A solution of 2-(1-Cyclobutyl-piperidin-4-yloxy)-6,7-dihydro-4H-thiazolo[5,4-c]pyridine-5-carboxylic acid tert-butyl ester (2.0 grams, 5 mmol, obtained in above step) in dichloromethane (30 mL) was treated with trifluroacetic acid (5.0 mL, 50 mmol) at 0° C. Reaction mass was stirred for 4 hours. After completion of reaction, the reaction mass was quenched into ice cold water and adjust pH to 10, by using 40% aqueous sodium hydroxide solution. The product was extracted with dichloromethane (3×50 mL), combined organics were washed with water followed by brine and dried over anhydrous sodium sulphate. Organic volatiles were evaporated under vacuum to obtain the title compound (1.3 grams).

$^1$H-NMR (δ ppm): 1.68-1.74 (2H, m), 1.85-1.93 (4H, m), 2.06 (4H, m), 2.19 (2H, m), 2.60-2.61 (4H, m), 2.73-2.80 (1H, m), 2.90-3.10 (1H, m), 3.13-3.16 (2H, m), 3.85 (2H, s), 4.90-4.93 (1H, m);

Mass (m/z): 294.2 $(M+H)^+$.

Step (iii): Preparation of 1-[2-(1-Cyclobutyl-piperidin-4-yloxy)-6,7-dihydro-4H-thiazolo[5,4-c]pyridin-5-yl]-propan-1-one A solution of 2-(1-Cyclobutyl-piperidin-4-yloxy)-4,5,6,7-tetrahydro-thiazolo[5,4-c]pyridine (1.3 grams, 4 mmol, obtained in above step) and triethylamine (1.9 mL, 13 mmol) in dichloromethane (30 mL) was cooled to 0° C. Propionyl-chloride (0.4 mL, 5 mmol) in dichloromethane (5 mL) was added drop wise over a period of 15 minutes and stirred the reaction for 30 minutes. Reaction mass was poured onto ice cold water and the product was extracted with ethyl acetate (3×50 mL). Combined organics were washed with water followed by brine and dried over anhydrous sodium sulphate. Organic volatiles were evaporated under vacuum. The residue was purified by flash chromatography (methanol/chloroform, 2/98) to obtain the title compound (1.0 gram).

$^1$H-NMR (δ ppm): 1.17-1.21 (3H, m), 1.65-1.72 (5H, m), 1.87-1.91 (4H, m), 2.01-2.07 (4H, m), 2.22 (1H, m), 2.38-2.45 (2H, m), 2.45 (1H, m), 2.68-2.76 (3H, m), 3.72-3.74 (1H, m), 4.47-4.62 (2H, m), 4.92-4.94 (1H, m).

Mass (m/z): 350.4 $(M+H)^+$.

Step (iv): Preparation of 1-[2-(1-Cyclobutyl-piperidin-4-yloxy)-6,7-dihydro-4H-thiazolo[5,4-c]pyridin-5-yl]-propan-1-one tartrate A solution of 1-[2-(1-Cyclobutyl-piperidin-4-yloxy)-6,7-dihydro-4H-thiazolo[5,4-c]pyridin-5-yl]-propan-1-one (0.8 grams, 2.3 mmol, obtained in above step) in methanol (10 mL) was treated with L(+)-Tartaric acid (0.34 grams, 2.3 mmol) at 0° C. Stirred the reaction mass for about 1 hour and the solvent was evaporated under vacuum to dryness. The solids were washed with diethyl ether and dried under vacuum to obtain the title compound (1.1 grams).

$^1$H-NMR (δ ppm): 1.12-1.20 (3H, m), 1.82-1.87 (2H, m), 2.16-2.32 (7H, m), 2.45-2.55 (2H, m), 2.63-2.66 (3H, m), 2.72 (1H, m), 3.20 (2H, m), 3.47-3.50 (1H, m), 3.66-3.70 (1H, m), 3.81-3.88 (2H, m), 4.45 (2H, s), 4.60 (2H, s), 5.18 (5H, m);

Mass (m/z): 350.4 $(M+H)^+$.

Example 2

Preparation of [2-(4-Cyclobutyl-cyclohexyloxy)-4,5,7,8-tetrahydro-thiazolo[5,4-d]azepin-6-yl]-cyclopropyl-methanone tartrate

Step (i): Preparation of 1-Cyclopropanecarbonyl-azepan-4-one

A solution of Azepan-4-one (1.75 grams, 15.3 mmol) and triethylamine (6.45 ml, 3.1 mmol) in dichloromethane (15 mL) was cooled to 0° C. Cyclopropionylchloride (0.17 mL, 1.8 mmol) in dichloromethane (2 mL) was added and stirred the reaction for 30 minutes. Reaction mass was poured onto ice cold water and the product was extracted with dichloromethane (3×15 mL). The combined organics were washed with water followed by brine and dried over anhydrous sodium sulphate. Organic volatiles were evaporated under vacuum to obtain the title compound (2.7 grams).

$^1$H-NMR (δ ppm): 0.66-0.69 (4H, m), 1.56-1.57 (1H, m), 1.71-1.75 (1H, m), 1.87-1.89 (1H, m), 2.45-2.49 (1H, m), 2.59-2.62 (1H, m), 3.57-3.91 (4H, m);

Mass (m/z): 182 (M+H)$^+$.

Step (ii): Preparation of 5-Bromo-1-cyclopropanecarbonyl-azepan-4-one

A solution of 1-Cyclopropanecarbonyl-azepan-4-one (2.7 grams, 14.9 mmol, obtained in above step) in acetic acid (30 mL) was cooled to 10° C. and treated with bromine (0.71 mL, 14.9 mmol) over a period of 15 minutes. The resulting slurry was stirred for 18 hours under nitrogen atmosphere. After completion of reaction, mass was concentrated to dryness to obtain the title compound (3.87 grams).

Mass (m/z): 260, 262 (M+H)$^+$.

Step (iii): Preparation of (2-Amino-4,5,7,8-tetrahydro-thiazolo[5,4-d]azepin-6-yl)-cyclopropyl-methanone A suspension of 5-Bromo-1-cyclopropanecarbonyl-azepan-4-one (3.87 grams, 14.8 mmol, obtained in above step) and thiourea (1.13 grams, 14.8 mmol) in isopropanol (40 mL) was refluxed for 6 hours. After completion of reaction, reaction mass was concentrated and the residue obtained was purified by flash chromatography (methanol/chloroform, 3/97) to obtain the title compound (0.4 grams).

$^1$H-NMR (δ ppm): 0.66-0.73 (4H, m), 1.95 (1H, m), 2.66-2.69 (2H, m), 2.75-2.76 (2H, m), 3.55-3.62 (2H, m), 3.79-3.86 (2H, m), 6.61 (2H, bs);

Mass (m/z): 238 (M+H)$^+$.

Step (iv): Preparation of (2-Bromo-4,5,7,8-tetrahydro-thiazolo[5,4-d]azepin-6-yl)-cyclopropyl-methanone A solution of (2-Amino-4,5,7,8-tetrahydro-thiazolo[5,4-d]azepin-6-yl)-cyclopropyl-methanone (0.4 grams, 1.68 mmol, obtained in above step) and copper (II) bromide (0.37 grams, 1.68 mmol) in acetonitrile (40 mL) was cooled to 0° C. Tertiary butyl nitrite (0.2 mL, 1.68 mmol) was added drop wise over a period of 10 minutes at 0° C. The reaction mass was stirred for 30 minutes and the reaction mass was quenched with 3N hydrochloric acid solution. The product was extracted with ethyl acetate (3×15 mL) and the combined organics were washed with water followed by brine and dried over sodium sulphate. Organic volatiles were evaporated under vacuum. The residue, thus obtained, was purified by flash chromatography (ethylacetate/n-hexane, 7/3) to obtain the title compound (0.053 grams).

$^1$H-NMR (δ ppm): 0.71-0.75 (4H, m), 1.97 (1H, m), 2.86-2.92 (2H, m), 2.99-3.08 (2H, m), 3.61-3.86 (2H, m), 3.86-3.90 (2H, m);

Mass (m/z): 301 (M+H)$^+$.

Step (v): Preparation of [2-(4-Cyclobutylpiperidin-4yl-oxy)-4,5,7,8-tetrahydro-thiazolo[5,4-d]azepin-6-yl]-cyclopropyl-methanone 1-Cyclobutyl-piperidin-4-ol (0.04 grams, 0.26 mmol) in tetrahydrofuran (3 mL) was treated with cooled and stirred suspension of sodium hydride (0.021 grams, 0.51 mmol) in tetrahydrofuran (8 mL) slowly over the period of 5 minutes and the reaction mixture was stirred for 2 hours at room temperature. A solution of (2-Bromo-4,5,7,8-tetrahydro-thiazolo[5,4-d]azepin-6-yl)-cyclopropyl-methanone (0.053 grams, 0.17 mmol, obtained in above step) in tetrahydrofuran (3 mL) was added drop wise over a period of 5 minutes and refluxed for 15 hours. Reaction mass was quenched onto ice cold water and the product was extracted with ethyl acetate (3×10 mL). The combined organics were washed with water followed by brine and dried over anhydrous sodium sulphate. Organic volatiles were evaporated under vacuum. The residue obtained was purified by flash chromatography (methanol/chloroform 3/97) to obtain the title compound (0.05 grams).

$^1$H-NMR (δ ppm): 0.84-0.86 (4H, m), 0.91 (1H, m), 1.73-1.76 (2H, m), 1.86-1.93 (4H, m), 2.07-2.08 (5H, m), 2.63 (2H, m), 2.80-2.84 (2H, m), 2.93-2.99 (3H, m), 3.74-3.79 (2H, m), 3.94-4.00 (2H, m).

Mass (m/z): 376.4 (M+H)$^+$.

Step (vi): Preparation of [2-(1-Cyclobutyl-piperidin-4-yloxy)-4,5,7,8-tetrahydro-thiazolo[5,4-d]azepin-6-yl]-cyclopropyl-methanone tartrate A solution of [2-(4-Cyclobutyl-cyclohexyloxy)-4,5,7,8-tetrahydro-thiazolo[5,4-d]azepin-6-yl]-cyclopropyl-methanone (0.078 grams, 0.208 mmol, obtained in above step) in methanol (5 mL) was treated with L(+)-Tartaric acid (0.031 grams, 0.208 mmol) at 0° C. Stirred the reaction mass for about 1 hour and the solvent was evaporated under vacuum to dryness. The solids were washed with diethyl ether and dried under vacuum to obtain the title compound (0.1 gram).

$^1$H-NMR (δ ppm): 0.84-0.99 (4H, m), 1.83-1.90 (2H, m), 2.00-2.02 (1H, m), 2.18-2.23 (5H, m), 2.32-2.41 (2H, m), 2.82-2.87 (2H, m), 2.95-2.99 (2H, m), 3.13-3.20 (5H, m), 3.62-3.66 (1H, m), 3.74-3.79 (2H, m), 3.95-3.99 (2H, m), 4.43 (2H, s), 5.13 (1H, s).

Mass (m/z): 376.4 (M+H)$^+$.

Example 3

Preparation of N-[2-(1-Cyclobutyl-piperidin-4-yloxy)-4,5,6,7-tetrahydro-benzothiazol-6-yl]-propionamide

Step (i): Preparation of 2-Bromo-4,5,6,7-tetrahydro-benzothiazol-6-ylamine

A solution of (2-Bromo-4,5,6,7-tetrahydro-benzothiazol-6-yl)-carbamic acid tert-butyl ester (0.50 grams, 1.5 mmol, obtained in preparation 2) in dichloromethane (30 mL) was treated with trifluroacetic acid (1.1 mL, 15 mmol) at 0° C. Reaction mass was stirred for 4 hours. After completion of the reaction, the mass was quenched with ice cold water and adjusted pH to 10, by using 40% aqueous sodium hydroxide solution. The product was extracted with dichloromethane (3×50 mL) and the combined organics were washed with water followed by brine and dried over anhydrous sodium sulphate. The organic volatiles were evaporated under vacuum to obtain the title compound (0.36 grams).

Mass (m/z): 233.0 (M+H)$^+$, 235.0 (M+3H)$^+$.

Step (ii): Preparation of N-(2-Bromo-4,5,6,7-tetrahydro-benzothiazol-6-yl)-propionamide A solution of 2-Bromo-4,5,6,7-tetrahydro-benzothiazol-6-ylamine (0.36 grams, 1.5 mmol, obtained in above step) and triethylamine (0.43 mL, mmol) in dichloromethane (15 mL) was cooled to 0° C. Propionylchloride (0.17 mL, 1.8 mmol) in dichloromethane (2 mL) were added and stirred the reaction mass for 30 minutes. After completion of reaction, the mass was poured onto ice cold water and the product was extracted with ethyl acetate (3×15 mL). The combined organics were washed with water followed by brine, dried over anhydrous sodium sulphate and the organic volatiles were evaporated under vacuum. The residue was purified by flash chromatography (methanol/chloroform, 2/98) to obtain the title compound (0.4 grams).

$^1$H-NMR (δ ppm): 0.81-0.85 (1H, m), 1.14-1.18 (3H, m), 1.20-1.28 (2H, m), 1.90-1.96 (1H, m), 2.02-2.05 (1H, m), 2.18-2.23 (2H, m), 2.57-2.63 (1H, m), 2.86-2.91 (1H, m), 3.10-3.15 (1H, m);

Mass (m/z): 289.2 (M+H)$^+$, 291.2 (M+3H)$^+$.

Step (iii): Preparation of N-[2-(1-Cyclobutyl-piperidin-4-yloxy)-4,5,6,7-tetrahydro-benzothiazol-6-yl]-propionamide 1-Cyclobutyl-piperidin-4-ol (0.25 grams, 1.6 mmol) in N,N-dimethyl formamide (5 mL) was treated with cooled and stirred suspension of sodium hydride (0.1 grams, 2.08 mmol) in N,N-dimethyl formamide (10 mL) slowly over the period of 30 minutes and the reaction mixture was further stirred for 1 hour. A solution of N-2-Bromo-4,5,6,7-tetrahydro-benzothiazol-6-yl)-propionamide (0.4 grams, 1.3 mmol, obtained in above step) in N,N-dimethyl formamide (5 mL) was added drop wise over a period of 10 minutes and stirred the resulting mass for 48 hours. After completion of reaction, the mass was quenched onto ice cold water and the product was extracted with ethyl acetate (3×15 mL). The combined organics were washed with water followed by brine, dried over anhydrous sodium sulphate, and the organic volatiles were evaporated under vacuum. The residue was purified by flash chromatography (ethylacetate/n-hexane, 1/1) to obtain the title compound (0.068 grams).

$^1$H-NMR (δ ppm): 0.81-0.88 (2H, m), 1.14-1.18 (3H, m), 1.65-1.70 (2H, m), 1.89-1.91 (5H, m), 2.03-2.05 (5H, m), 2.17-2.23 (3H, m), 2.49-2.75 (4H, m), 2.96-3.01 (2H, m), 4.35-4.39 (1H, m), 4.90-3.96 (1H, m), 5.50-5.53 (1H, m);

Mass (m/z): 364.3 (M+H)$^+$.

Examples 4-34

The compounds of Examples 4-34 were prepared by following the procedures as described in Examples 1 to 3, with some non-critical variations

| | | |
|---|---|---|
| 4. | [2-(1-Cyclobutyl-piperidin-4-yloxy)-6,7-dihydro-4H-thiazolo[5,4-c]pyridin-5-yl]-cyclopropyl-methanone tartrate | $^1$H - NMR (δ ppm): 0.86-0.90 (5H, m), 1.27-1.29 (2H, m), 1.82-1.90 (2H, m), 2.01-2.11 (1H, m), 2.25-2.31 (7H, m), 2.64 (1H, m), 2.77 (1H, m), 3.20 (3H, bs), 3.65-3.69 (1H, m), 3.88 (1H, m), 4.04-4.06 (1H, m), 4.44 (2H, m), 4.60 (1H, s), 5.19 (1H, m); Mass (m/z): 362.2 (M + H)$^+$. |
| 5. | Cyclobutyl-[2-(1-cyclobutyl-piperidin-4-yloxy)-6,7-dihydro-4H-thiazolo[5,4-c]pyridin-5-yl]-methanone tartrate | $^1$H - NMR (δ ppm): 1.27-1.38 (2H, m), 1.81-1.88 (3H, m), 2.00-2.10 (1H, m), 2.20-2.33 (11H, m), 2.68 (1H, m), 3.19 (3H, m), 3.33-3.36 (1H, m), 3.52 (1H, m), 3.67-3.73 (2H, m), 3.86 (1H, m), 4.44 (2H, s), 4.47 (1H, s), 4.58 (1H, s), 5.18 (1H, m); Mass (m/z): 376.3 (M + H)$^+$. |
| 6. | [2-(1-Cyclobutyl-piperidin-4-yloxy)-6,7-dihydro-4H-thiazolo[5,4-c]pyridin-5-yl]-(2-fluoro-phenyl)-methanone tartrate | $^1$H - NMR (δ ppm): 1.83-1.91 (2H, m), 2.16 (2H, s), 2.22-2.25 (5H, m), 2.33 (3H, m), 2.78 (1H, m), 3.13-3.20 (4H, m), 3.65-3.70 (2H, m), 4.08 (1H, m), 4.43-4.45 (3H, m), 5.19 (1H, bs), 7.23-7.34 (2H, m), 7.40-7.43 (1H, m), 7.53 (1H, m); Mass (m/z): 416.3 (M + H)$^+$. |
| 7. | 1-[2-(1-Cyclobutyl-piperidin-4-yloxy)-6,7-dihydro-4H-thiazolo[5,4-c]pyridin-5-yl]-3-methyl-butan-1-one tartrate | $^1$H - NMR (δ ppm): 0.94-1.00 (7H, m), 1.85-1.91 (2H, m), 2.05-2.16 (7H, m), 2.21-2.38 (4H, m), 2.64-2.72 (2H, m), 3.18 (4H, m), 3.63-3.67 (1H, m), 3.83-3.90 (2H, m), 4.44 (2H, s), 4.61 (1H, s), 5.18 (1H, m); Mass (m/z): 378.2 (M + H)$^+$. |
| 8. | Cyclobutyl-[2-(1-isopropyl-piperidin-4-yloxy)-6,7-dihydro-4H-thiazolo[5,4-c]pyridin-5-yl]-methanone | $^1$H - NMR (δ ppm): 1.43 (7H, m), 1.87-1.89 (1H, m), 1.97-2.04 (1H, m), 2.19-2.24 (2H, m), 2.33-2.41 (4H, m), 2.62 (2H, bs), 2.76 (1H, m), 3.07 (2H, m), 3.25-3.26 (3H, m), 3.43-3.50 (1H, m), 3.62-3.65 (3H, m), 4.61 (1H, s), 5.23 (1H, m); Mass (m/z): 364.2 (M + H)$^+$. |
| 9. | Cyclopropyl-[2-(1-isopropyl-piperidin-4-yloxy)-6,7-dihydro-4H-thiazolo[5,4-c]pyridin-5-yl]-methanone tartrate | $^1$H - NMR (δ ppm): 0.86-0.90 (4H, m), 1.27-1.39 (7H, m), 1.98-2.08 (2H, m), 2.30 (3H, m), 2.64-2.77 (2H, m), 3.13 (2H, m), 3.48 (2H, m), 3.52-3.57 (1H, m), 3.88 (1H, m), 4.05 (1H, m), 4.45 (2H, s), 4.68 (1H, s), 5.19 (1H, m); Mass (m/z): 350.4 (M + H)$^+$. |
| 10. | Cyclopropyl-[2-(1-cyclopropyl-piperidin-4-yloxy)-6,7-dihydro-4H-thiazolo[5,4-c]pyridin-5-yl]-methanone tartrate | $^1$H - NMR (δ ppm): 0.79-0.91 (8H, m), 1.99-2.18 (5H, m), 2.39 (1H, bs), 2.64-2.77 (3H, m), 3.12 (2H, bs), 3.28 (2H, s), 3.88 (1H, bs), 4.05 (1H, m), 4.45 (2H, s), 4.60 (1H, s), 5.08 (1H, bs); Mass (m/z): 348.2 (M + H)$^+$. |
| 11. | Cyclobutyl-[2-(1-cyclopropyl-piperidin-4-yloxy)-6,7-dihydro-4H-thiazolo[5,4-c]pyridin-5-yl]-methanone tartrate | $^1$H - NMR (δ ppm): 0.76-0.77 (3H, m), 0.87-0.92 (2H, m), 1.80-1.87 (2H, m), 2.02-2.03 (3H, m), 2.21-2.33 (6H, m), 2.63-2.67 (2H, m), 3.05 (1H, m), 3.21-3.23 (2H, m), 3.43-3.52 (2H, m), 3.71-3.73 (1H, m), 3.85-3.88 (1H, m), 4.43 (2H, s), 4.58 (1H, s), 5.05 (1H,m); Mass (m/z): 362.2 (M + H)$^+$. |

| | | |
|---|---|---|
| 12. | 1-[2-(1-Cyclobutyl-piperidin-4-yloxy)-6,7-dihydro-4H-thiazolo[5,4-c]pyridin-5-yl]-2-morpholin-4-yl-ethanone tartrate | $^1$H - NMR (δ ppm): 1.27-1.31 (1H, m), 1.81-1.89 (2H, m), 2.21-2.32 (8H, m), 2.52-2.56 (4H, m), 2.65 (1H, m), 2.78 (1H, m), 3.13-3.20 (4H, m), 3.39 (1H, s), 3.60-3.64 (2H, m), 3.70-3.72 (3H, m), 3.87-3.90 (2H, m), 4.41 (2H, s), 4.60 (1H, s), 4.71 (1H, s), 5.17 (1H, bs);<br>Mass (m/z): 421.4 (M + H)$^+$. |
| 13. | [4-(5-Cyclobutyl-,6,7-dihydro-4H-thiazolo[5,4-c]pyridin-2-yloxy)-piperidin-1-yl]-cyclopropyl-methanone tartrate | $^1$H - NMR (δ ppm): 0.80-0.88 (4H, m), 1.27-1.29 (2H, d), 1.38 (1H, s), 1.85-1.90 (3H, m), 1.99 (2H, m), 2.17-2.20 (3H, m), 2.31 (3H, m), 2.89-2.90 (2H, m), 3.24-3.28 (3H, m), 3.35 (1H, s), 3.62-3.64 (2H, m), 4.01 (2H, s), 5.16-5.19 (1H, m);<br>Mass (m/z): 362.3 (M + H)$^+$. |
| 14. | [3-(5-Cyclobutyl-,6,7-dihydro-4H-thiazolo[5,4-c]pyridin-2-yloxy)-piperidin-1-yl]-cyclopropyl-methanone tartrate | $^1$H - NMR (δ ppm): 0.60-0.79 (1H, m), 0.81-0.91 (4H, m), 1.16-1.29 (1H, m), 1.56 (1H, m), 1.78 (1H, m), 1.89-2.06 (4H, m), 2.29 (2H, m), 2.41-2.43 (2H, m), 2.98 (2H, m), 3.13 (1H, m), 3.60 (1H, m), 3.70 (1H, m), 3.90-3.91 (2H, m), 4.09 (2H, m), 4.35-4.50 (1H, m), 4.54 (2H, s), 4.95-4.96 (1H, m);<br>Mass (m/z): 362.3 (M + H)$^+$. |
| 15. | [2-(1-Cyclobutyl-piperidin-3-yloxy)-6,7-dihydro-4H-thiazolo[5,4-c]pyridin-5-yl]-cyclopropyl-methanone tartrate | $^1$H - NMR (δ ppm): 0.81-0.91 (4H, m), 1.80-1.87 (3H, m), 1.98-2.10 (5H, m), 2.24-2.28 (3H, m), 2.61 (1H, m), 2.78 (1H, m), 2.80 (1H, m), 3.20-3.21 (2H, m), 3.53 (1H, m), 3.88 (1H, bs), 4.05 (1H, m), 4.43 (2H, s), 4.61 (1H, s), 4.84-4.85 (2H, m), 5.27 (1H, bs);<br>Mass (m/z): 362.3 (M + H)$^+$. |
| 16. | [2-(1-Cyclobutyl-piperidin-4-yloxy)-6,7-dihydro-4H-thiazolo[5,4-c]pyridin-5-yl]-pyridin-4-yl-methanone tartrate | $^1$H - NMR (δ ppm): 1.79-1.88 (2H, m), 2.30-2.32 (8H, m), 2.71 (1H, m), 2.79 (1H, s), 3.18-3.23 (4H, m), 3.62-3.67 (2H, m), 3.67 (1H, m), 4.44 (3H, s), 4.46 (1H, s), 5.20 (1H, bs), 7.48-7.51 (2H, m), 8.69 (2H, m);<br>Mass (m/z): 399.6 (M + H)$^+$. |
| 17. | [2-(1-Cyclobutyl-piperidin-4-yloxy)-6,7-dihydro-4H-thiazolo[5,4-c]pyridin-5-yl]-(4-methoxy-phenyl)-methanone tartrate | $^1$H - NMR (δ ppm): 1.27-1.29 (1H, m), 1.81-1.90 (2H, m), 2.24-2.31 (8H, m), 2.74 (2H, m), 3.13-3.17 (3H, m), 3.62-3.66 (1H, m), 3.82-3.83 (1H, m), 3.85 (3H, s), 3.90-4.10 (1H, bs), 4.43 (2H, s), 4.67 (2H, m), 5.18 (1H, m), 7.01-7.03 (2H, d), 7.43-7.45 (2H, d);<br>Mass (m/z): 428.3 (M + H)$^+$. |
| 18. | 1-[2-(1-Cyclobutyl-piperidin-4-yloxy)-6,7-dihydro-4H-thiazolo[5,4-c]pyridin-5-yl]-2-piperidin-1-yl-ethanone tartrate | $^1$H - NMR (δ ppm): 1.66 (2H, bs), 1.83-1.87 (6H, m), 2.16 (2H, m), 2.22-2.26 (5H, m), 2.68-2.78 (3H, m), 3.09-3.16 (8H, m), 3.49-3.51 (1H, m), 3.75 (1H, m), 3.91 (1H, m), 4.08-4.14 (2H, d), 4.40 (2H, s), 4.55 (1H, s), 4.65 (1H, s), 5.49 (1H, s);<br>Mass (m/z): 419.5 (M + H)$^+$. |
| 19. | 1-[2-(1-Cyclobutyl-piperidin-4-yloxy)-6,7-dihydro-4H-thiazolo[5,4-c]pyridin-5-yl]-2-cyclopropyl-ethanone | $^1$H - NMR (δ ppm): 0.17-0.21 (2H, m), 0.57-0.60 (2H, m), 1.09 (1H, m), 1.26-1.29 (2H, m), 1.63-1.72 (4H, m), 1.85-1.90 (4H, m), 2.03-2.05 (4H, m), 2.20 (2H, bs), 2.32-2.38 (2H, m), 2.57 (2H, bs), 2.71-2.73 (2H, m), 3.72-3.75 (1H, m), 4.92 (1H, m);<br>Mass (m/z): 376.3 (M + H)$^+$. |
| 20. | 2-(1-Cyclobutyl-piperidin-4-yloxy)-5-(2-fluoro-benzenesulfonyl)-,6,7-dihydro-4H-thiazolo[5,4-c]pyridine tartrate | $^1$H - NMR (δ ppm): 1.83-1.91 (2H, m), 2.21-2.25 (6H, m), 2.30-2.34 (2H, m), 2.60-2.62 (2H, m), 3.31-3.18 (3H, m), 3.64-3.69 (3H, m), 4.40 (2H, s), 4.45 (3H, s), 5.1 (1H, m), 7.27-7.31 (1H, m), 7.35-7.39 (1H, m), 7.65-7.68 (1H, m), 7.90-7.94 (1H, m);<br>Mass (m/z): 452.2 (M + H)$^+$. |
| 21. | 2-(1-Cyclobutyl-piperidin-4-yloxy)-5-methanesulfonyl-,6,7-dihydro-4H-thiazolo[5,4-c]pyridine | $^1$H - NMR (δ ppm): 1.42 (1H, s), 1.66-1.73 (2H, m), 1.88 (4H, m), 2.04-2.05 (4H, m), 2.20 (2H, m), 2.59 (1H, m), 2.74-2.79 (3H, m), 2.86 (3H, s), 3.64-3.67 (2H, t), 4.38 (2H, s), 4.92-4.97(1H, m);<br>Mass (m/z): 372.3 (M + H)$^+$. |
| 22. | 1-[2-(1-Cyclobutyl-piperidin-4-yloxy)-6,7-dihydro-4H-thiazolo[5,4-c]pyridin-5-yl]-2-methyl-propan-1-one tartrate | $^1$H - NMR (δ ppm): 1.08-1.10 (6H, m), 1.13-1.18 (4H, m), 1.81-1.89 (2H, m), 2.20-2.29 (7H, m), 2.64-2.66 (1H, m), 2.73 (1H, m), 3.13 (3H, m), 3.35 (1H, s), 3.58-3.62 (1H, t), 3.87-3.89 (1H, m), 4.41 (2H, s), 4.60 (1H, s), 4.66 (1H, s);<br>Mass (m/z): 364.2 (M + H)$^+$. |
| 23. | 2-(1-Cyclobutyl-piperidin-4-yloxy)-5-(2-trifluoromethyl-pyridin-5-yl)-,6,7-dihydro-4H-thiazolo[5,4-c]pyridine | $^1$H - NMR (δ ppm): 1.56-1.77 (7H, m), 1.95-1.98 (4H, s), 2.04 (2H, m), 2.48-2.49 (1H, m), 2.68-2.69 (3H, m), 3.79-3.82 (2H, m), 4.49 (2H, s), 4.82-4.84 (1H, m), 7.49-7.52 (1H, dd), 7.63-7.65 (1H, d), 8.48-8.49 (1H, d);<br>Mass (m/z): 439.2 (M + H)$^+$. |
| 24. | Cyclopropyl-[2-(1-isobutyl-piperidin-4-yloxy)-6,7-dihydro-4H-thiazolo[5,4-c]pyridin-5-yl]-methanone tartrate | $^1$H - NMR (δ ppm): 0.86-0.90 (4H, m), 1.05-1.07 (6H, d), 1.29 (1H, m), 1.90 (1H, m), 2.10 (1H, m), 2.30 (3H, m), 2.77 (2H, m), 2.99-3.01 (2H, d), 3.10 (1H, m), 3.48 (2H, m), 3.88-4.07 (2H, m), 4.46 (2H, s), 4.60 (1H, s), 4.84-4.86 (2H, m), 5.18 (1H, m);<br>Mass (m/z): 363.5 (M + H)$^+$. |
| 25. | [2-(1-Cyclobutyl-piperidin-4-yloxy)-6,7-dihydro-4H-thiazolo[5,4-c]pyridin-5-yl]-(2-trifluoromethyl-pyridin-5-yl)-methanone tartrate | $^1$H - NMR (δ ppm): 1.62-1.67 (4H, m), 1.69-1.72 (3H, m), 1.93 (4H, m), 2.07 (3H, m), 2.28 (1H, m), 2.61-2.62 (1H, m), 2.74-2.84 (2H, m), 3.50 (1H, s), 3.68 (1H, m), 4.79 (1H, bs), 4.98 (1H, m), 7.79-7.81 (1H, d), 7.98-8.00 (1H, d), 8.82 (1H, bs);<br>Mass (m/z): 467.3 (M + H)$^+$. |
| 26. | [2-(1-Cyclobutyl-piperidin-4-yloxy)-6,7-dihydro-4H-thiazolo[5,4-c]pyridin-5-yl]-pyridin-3-yl-methanone tartrate | $^1$H - NMR (δ ppm): 1.79-1.88 (2H, m), 2.16-2.20 (2H, m), 2.26-2.31 (4H, m), 2.74-2.79 (2H, m), 3.13-3.19 (4H, m), 3.35 (2H, s), 3.62-3.68 (1H, m), 3.72 (1H, bs), 4.07 (1H, m), 4.43 (2H, s), 4.55 (1H, bs), 4.78 (1H, s), 5.19 (1H, bs), 7.56 (1H, m), 7.95-7.97 (1H, d), 8.67 (2H, s);<br>Mass (m/z): 398.5 (M + H)$^+$. |

| | | |
|---|---|---|
| 27. | 2-(1-Cyclobutyl-piperidin-4-yloxy)-5-pyridin-3-yl-,6,7-dihydro-4H-thiazolo[5,4-c]pyridine tartrate | $^1$H - NMR (δ ppm): 1.83-1.88 (2H, m), 2.21-2.32 (7H, m), 2.65-2.75 (2H, m), 3.13-3.25 (5H, m), 3.60-3.62 (2H, m), 3.73-3.76 (2H, t), 4.38 (2H, s), 7.29-7.32 (1H, dd, J = 4.62, 8.42 Hz), 7.48-7.50(1H, d, J = 8.07 Hz), 7.97-7.98 (1H, d, J = 4.21 Hz), 8.29 (1H, s);<br>Mass (m/z): 371.3 (M + H)$^+$. |
| 28. | [2-(1-Cyclobutyl-piperidin-4-yloxy)-6,7-dihydro-4H-thiazolo[5,4-c]pyridin-5-yl]-(tetrahydro-pyran-4-yl)-methanone | $^1$H - NMR (δ ppm): 1.13-1.19 (1H, t), 1.22 (1H, s), 1.54-1.74 (9H, m), 1.88 (1H, s), 1.93-1.95 (5H, m), 2.64-2.67 (3H, m), 3.32-3.42 (4H, m), 3.73-3.84 (4H, m), 4.48 (1H, s), 4.62 (1H, s), 4.71-4.90 (1H, m);<br>Mass (m/z): 406.3 (M + H)$^+$. |
| 29. | [2-(1-Cyclobutyl-piperidin-4-yloxy)-6,7-dihydro-4H-thiazolo[5,4-c]pyridin-5-yl]-morpholin-4-yl-methanone tartrate | $^1$H - NMR (δ ppm): 1.84-1.98 (3H, m), 2.16-2.32 (9H, m), 2.70-2.71 (2H, t), 3.13-3.25 (6H, m), 3.56-3.61 (3H, t), 3.67-3.69 (4H, t), 4.33 (2H, s), 4.42 (2H, s), 5.12-5.22 (1H, m);<br>Mass (m/z): 407.3 (M + H)$^+$. |
| 30. | [2-(1-Cyclobutyl-piperidin-4-yloxy)-6,7-dihydro-4H-thiazolo[5,4-c]pyridin-5-yl]-piperidin-1-yl-methanone hydrochloride | $^1$H - NMR (δ ppm): 1.59-1.65 (6H, m), 1.85-1.88 (2H, m), 2.22-2.27 (4H, t), 2.29-2.33 (2H, t), 2.69-2.72 (2H, t), 3.13-3.17 (3H, m), 3.28-3.35 (5H, m), 3.52-3.55 (3H, t), 3.65-3.75 (1H, m), 4.29 (2H, s), 4.43 (2H, s), 5.12-5.22 (1H, m);<br>Mass (m/z): 405.4 (M + H)$^+$. |
| 31. | 6-[2-(1-Cyclobutyl-piperidin-4-yloxy)-6,7-dihydro-4H-thiazolo[5,4-c]pyridin-5-yl]-nicotinamide | $^1$H - NMR (δ ppm): 1.82-1.99 (2H, m), 2.25-2.33 (8H, m), 2.74-2.76 (2H, m), 3.14-3.25 (4H, m), 3.62-3.66 (1H, m), 4.03-4.06 (2H, t), 4.43 (2H, s), 4.73 (2H, s), 4.99-5.16 (1H, m), 6.91-6.93 (1H, d, J = 9.03 Hz), 8.01-8.03 (1H, dd , J = 2.40, 9.00 Hz), 8.65-8.66 (1H, d, J = 2.28 Hz);<br>Mass (m/z): 414.3 (M + H)$^+$. |
| 32. | [2-(1-Cyclobutyl-piperidin-4-yloxy)-6,7-dihydro-4H-thiazolo[5,4-c]pyridin-5-yl]-cyclopentyl-methanone tartrate | $^1$H - NMR (δ ppm): 1.27-1.29 (2H, m), 1.38 (1H, s), 1.62-1.64 (2H, m), 1.71-1.74 (4H, m), 1.78-1.90 (4H, m), 2.21-2.25 (4H, m), 2.30-2.34 (2H, m), 2.60 (1H, m), 2.72 (1H, m), 3.13-3.18 (4H, m), 3.66 (1H, m), 3.66-3.91 (2H, m), 4.44 (2H, s), 4.60-4.66 (2H, d), 5.18 (1H, m);<br>Mass (m/z): 390.5 (M + H)$^+$. |
| 33. | [2-(1-Cyclobutyl-piperidin-4-yloxy)-6,7-dihydro-5H-thiazolo[5,4-b]pyridin-4-yl]-cyclopropyl-methanone tartrate | $^1$H - NMR (δ ppm): 0.86-0.90 (5H, m), 1.27-1.29 (2H, m), 1.82-1.90 (2H, m), 2.01-2.11 (1H, m), 2.25-2.31 (7H, m), 2.64 (1H, m), 2.77 (1H, m), 3.20(3H, bs), 3.65-3.69 (1H, m), 3.88 (1H, m), 4.04-4.06 (1H, m), 4.44 (2H, m), 4.60 (1H, s), 5.19 (1H, m);<br>Mass (m/z): 362.2 (M + H)$^+$. |
| 34. | Cyclopropyl-[2-(1-isopropyl-piperidin-4-yloxy)-4,5,7,8-tetrahydro-thiazolo[5,4-d]azepin-6-yl]-methanone tartrate | $^1$H - NMR (δ ppm): 0.84-0.91 (4H, m), 1.27-1.29 (1H, m), 1.37-1.41 (7H, m), 2.00-2.02 (1H, m), 2.21-2.31 (4H, m), 2.81-2.88 (2H, m), 2.96-3.01 (2H, m), 3.51-3.61 (2H, m), 3.72-3.79 (2H, m), 3.93-3.99 (2H, m), 4.40-4.55 (3H, m), 5.13 (1H, s);<br>Mass (m/z): 364 (M + H)$^+$. |

Examples 35-66

The person skilled in the art can prepare the compounds of Examples 35-66 by following the procedures described above.

35. [2-(1-Cyclobutyl-piperidin-4-yloxy)-6,7-dihydro-5H-thiazolo[5,4-b]pyridin-4-yl]-cyclopropyl-methanone
36. 1-[2-(1-Cyclobutyl-piperidin-4-yloxy)-6,7-dihydro-5H-thiazolo[5,4-b]pyridin-4-yl]-propan-1-one
37. Cyclobutyl-[2-(1-cyclobutyl-piperidin-4-yloxy)-6,7-dihydro-5H-thiazolo[5,4-b]pyridin-4-yl]-methanone
38. N-[2-(1-Cyclobutyl-piperidin-4-yloxy)-4,5,6,7-tetrahydro-benzothiazol-7-yl]-propionamide
39. 1-[2-(1-Cyclobutyl-piperidin-4-yloxy)-6,7-dihydro-4H-oxazolo[5,4-c]pyridin-5-yl]-propan-1-one
40. 1-[2-(1-Cyclobutyl-piperidin-4-yloxy)-4,6-dihydro-pyrrolo[4,3-d]oxazol-5-yl]-propan-1-one
41. N-[2-(1-Cyclobutyl-piperidin-4-yloxy)-5,6-dihydro-4H-cyclopentaoxazol-5-yl]-propionamide
42. N-[2-(1-Cyclobutyl-piperidin-4-yloxy)-5,6-dihydro-4H-cyclopentathiazol-5-yl]-propionamide
43. 1-[2-(1-Cyclobutyl-piperidin-4-yloxy)-4,6-dihydro-pyrrolo[4,3-d]thiazol-5-yl]-propan-1-one
44. 1-[2-(1-Cyclobutyl-piperidin-4-yloxy)-5,6-dihydro-pyrrolo[3,2-d]thiazol-4-yl]-propan-1-one
45. N-[2-(1-Cyclobutyl-piperidin-4-yloxy)-5,6-dihydro-4H-cyclopentathiazol-6-yl]-propionamide
46. N-[2-(1-Cyclobutyl-piperidin-4-yloxy)-5,6-dihydro-4H-cyclopentaoxazol-6-yl]-propionamide
47. 1-[2-(1-Cyclobutyl-piperidin-4-yloxy)-5,6-dihydro-pyrrolo[3,2-d]oxazol-4-yl]]-propan-1-one
48. 1-[2-(1-Cyclobutyl-piperidin-4-yloxy)-4,6-dihydro-pyrrolo[4,3-d]oxazol-5-yl]-propan-1-one
49. N-[2-(1-Cyclobutyl-piperidin-4-yloxy)-5,6-dihydro-4H-cyclopentaoxazol-5-yl]-propionamide
50. 1-[2-(1-Cyclobutyl-piperidin-4-yloxy)-4,6,7,8-tetrahydro-thiazolo[5,4-c]azepin-5-yl]-propan-1-one
51. 1-[2-(1-Cyclobutyl-piperidin-4-yloxy)-4-methyl-6,7-dihydro-4H-thiazolo[5,4-c]pyridin-5-yl]-propan-1-one
52. 1-[2-(1-Cyclobutyl-piperidin-4-yloxy)-7-fluoro-6,7-dihydro-4H-thiazolo[5,4-c]pyridin-5-yl]-propan-1-one
53. 1-[2-(1-Cyclobutyl-piperidin-4-yloxy)-7-methyl-6,7-dihydro-4H-thiazolo[5,4-c]pyridin-5-yl]-propan-1-one
54. 1-[2-(1-Cyclobutyl-piperidin-4-yloxy)-6-methyl-6,7-dihydro-4H-thiazolo[5,4-c]pyridin-5-yl]-propan-1-one
55. 1-[2-(1-Cyclobutyl-3-methyl-piperidin-4-yloxy)-6,7-dihydro-4H-thiazolo[5,4-c]pyridin-5-yl]-propan-1-one
56. 1-[2-(1-Cyclobutyl-3-fluoro-piperidin-4-yloxy)-6,7-dihydro-4H-thiazolo[5,4-c]pyridin-5-yl]-propan-1-one
57. 1-Cyclobutyl-4-(5-propionyl-4,5,6,7-tetrahydro-thiazolo[5,4-c]pyridin-2-yloxy)-piperidine-3-carbonitrile
58. 1-[2-(1-Cyclobutyl-azepan-4-yloxy)-6,7-dihydro-4H-thiazolo[5,4-c]pyridin-5-yl]-propan-1-one
59. 1-[2-(1-Cyclobutyl-azepan-4-yloxy)-4,5,7,8-tetrahydro-thiazolo[5,4-d]azepin-6-yl]-propan-1-one
60. 1-[2-(1-Cyclobutyl-pyrrolidin-3-yloxy)-4,5,7,8-tetrahydro-thiazolo[5,4-d]azepin-6-yl]-propan-1-one
61. 1-[2-(1-Cyclobutyl-pyrrolidin-3-yloxy)-4,6-dihydro-pyrrolo[4,3-d]thiazol-5-yl]-propan-1-one -continued 62. 1-[2-(1-Cyclobutyl-azepan-4-yloxy)-4,6-dihydro-pyrrolo[4,3-d]thiazol-5-yl]-propan-1-one
63. 1-{2-[1-(2-Hydroxy-ethyl)-piperidin-4-yloxy]-6,7-dihydro-4H-thiazolo[5,4-c]pyridin-5-yl}-propan-1-one
64. 1-[2-(1-Ethoxymethyl-piperidin-4-yloxy)-6,7-dihydro-4H-thiazolo[5,4-c]pyridin-5-yl]-propan-1-one
65. 1-{2-[1-(2,2,2-Trifluoro-ethyl)-piperidin-4-yloxy]-6,7-dihydro-4H-thiazolo[5,4-c]pyridin-5-yl}-propan-1-one
66. 1-[2-(1-Cyclobutyl-azetidin-3-yloxy)-6,7-dihydro-4H-thiazolo[5,4-c]pyridin-5-yl]-propan-1-one Biological Assays Example 67

Binding and Functional Assays for Human or Rat Histamine H3 Receptor

Compounds can be evaluated according to the following procedures.

Materials and Methods:
   Receptor source: Rat brain frontal cortex or recombinant human cDNA expressed in CHO cells
   Radioligand: [$^3$H] R-α-methylhistamine
   Final ligand concentration—[3.0 nM]
   Non-specific determinant: R-α-methylhistamine (100 uM)
   Reference compound: R-α-methylhistamine
   Positive control: R-α-methylhistamine Incubation Conditions:
   Increasing concentrations of test compounds or standard were incubated with membrane receptors and radioligand in 5 mM $MgCl_2$ and 50 mM TRIS-HCl (pH 7.4) for 60 minutes at room temperature. The reaction was terminated by rapid vacuum filtration onto the glass fiber filters. Radioactivity trapped onto the filters was determined and compared to the control values in order to ascertain any interactions of the test compound(s) with either cloned human or rat receptor binding site.

| Example Number | $K_i$ (nM) |
|---|---|
| 1. | 3.83 |
| 2. | 2.0 |
| 3. | 26.67 |
| 4. | 7.2 |
| 5. | 3.3 |
| 6. | 13.4 |
| 7. | 10.5 |
| 8. | 7.69 |
| 9. | 9.94 |
| 10. | 5.43 |
| 11. | 11.98 |
| 12. | 8.44 |
| 14. | 23.6 |
| 16. | 33.55 |
| 17. | 21.2 |
| 18. | 6.96 |
| 19. | 12.28 |
| 20. | 7.4 |
| 21. | 22.6 |
| 22. | 9.5 |
| 23. | 0.3 |
| 25. | 35.33 |
| 26. | 32.54 |
| 27. | 0.75 |
| 28. | 38.96 |
| 29. | 11.3 |
| 30. | 4.19 |
| 31. | 1.62 |
| 32. | 4.6 |
| 33. | 15.45 |
| 34. | 15.6 |

Literature Reference: Millipore data sheet.

Example 68

Rodent Pharmacokinetic Study

Male Wistar rats (230-280 grams) obtained from NIN (National Institute of Nutrition, Hyderabad, India) were used as an experimental animal. Three animals were housed in each cage. Animals were kept fasted over night and maintained on a 12 hours light/dark cycle. Three rats were dosed New chemical entity (NCE) orally (3 or 10 mg/kg) and intravenously (1 or 5 mg/kg) on day 0 and day 2.

At each time point blood was collected by jugular vein. Blood was stored at 2-8° C. until analysis. The concentrations of the NCE compound in blood were determined using LC-MS/MS method. Schedule time points: Pre dose 0.08, 0.25, 0.5, 1, 2, 4, 6, 8 and 24 hours after dosing (n=3). The NCE compounds were quantified in blood by partially validated LC-MS/MS method using acetonitrile precipitation technique. NCE compounds were quantified in the calibration range of 1-2000 ng/mL in blood. Study samples were analyzed using calibration samples in the batch and quality control samples spread across the batch.

Pharmacokinetic parameters were calculated by non-compartmental model using software WinNonlin version 5.0.1.

| Example Number | Strain/Gender | Dose (mg/kg) | Vehicle | Route of administration | $C_{max}$ (ng/mL) | $T_{max}$ (h) | $AUC_t$ (ng·hr/mL) | $T_{1/2}$ (h) | Bioavailability (%) |
|---|---|---|---|---|---|---|---|---|---|
| 1. | Wistar/Male | 1 | Water | Intravenous | 436 ± 118 | 0.08 ± 0.00 | 356 ± 61 | 0.98 ± 0.13 | 49 ± 5 |
|  |  | 3 | Water | Per Oral | 329 ± 23 | 0.42 ± 0.14 | 524 ± 51 | 0.95 ± 0.07 |  |
| 4. | Wistar/Male | 1 | Water | Intravenous | 320 ± 62 | 0.08 ± 0.00 | 348 ± 7 | 1.25 ± 0.11 | 39 ± 8 |
|  |  | 3 | Water | Per Oral | 199 ± 48 | 0.67 ± 0.29 | 407 ± 89 | 1.67 ± 0.21 |  |
| 5. | Wistar/Male | 1 | Water | Intravenous | 287 ± 58 | 0.08 ± 0.00 | 155 ± 38 | 0.43 ± 0.10 | 25 ± 1 |
|  |  | 3 | Water | Per Oral | 101 ± 37 | 0.42 ± 0.14 | 117 ± 34 | 0.57 ± 0.10 |  |
| 12. | Wistar/Male | 1 | Water | Intravenous | 237 ± 38 | 0.08 ± 0.00 | 334 ± 39 | 2.86 ± 0.82 | 43 ± 17 |
|  |  | 3 | Water | Per Oral | 151 ± 18 | 0.83 ± 0.29 | 417 ± 120 | 2.85 ± 0.38 |  |
| 22. | Wistar/Male | 1 | Water | Intravenous | 205 ± 47 | 0.08 ± 0.00 | 110 ± 15 | 0.5 ± 0.05 | 65 ± 24 |
|  |  | 3 | Water | Per Oral | 189 ± 56 | 0.42 ± 0.14 | 206 ± 56 | 0.54 ± 0.11 |  |
| 28. | Wistar/Male | 1 | Water | Intravenous | 370 ± 25 | 0.08 ± 0.00 | 282 ± 23 | 0.67 ± 0.06 | 82 ± 38 |
|  |  | 3 | Water | Per Oral | 286 ± 40 | 0.83 ± 0.29 | 701 ± 328 | 0.95 ± 0.28 |  |

Example 69

Rodent Brain Penetration Study

Male Wister rats (230-280 grams) obtained from NIN (National Institute of Nutrition, Hyderabad, India) was used as experimental animals. Three animals were housed in each cage. Animals were given water and food ad libitum throughout the experiment, and maintained on a 12 hours light/dark cycle.

New chemical entity (NCE) was dissolved in suitable vehicle and administered orally (3 or 10 mg/kg). Around $T_{max}$ (i.e, 0.5 hour, 1.0 hour and 2.0 hours) animals were sacrificed. Blood and brain tissue were collected and brain was homogenized to yield 20% w/v. Blood was stored at 2-8° C. and brain homogenate was frozen at −20° C. until analysis. The concentrations of NCE in blood and brain were quantified using LC-MS/MS method.

The NCE was quantified in blood and brain homogenate by partially validated LC-MS/MS method using acetonitrile precipitation technique. NCE compounds were quantified in the calibration range of 1-500 ng/mL in blood and brain homogenate. Study samples were analyzed using calibration samples in the batch and quality control samples spread across the batch. Extents of brain-blood ratio were calculated ($C_b/C_p$).

| Example Number | Strain/Gender | Dose (mg/kg) | Vehicle | Route of administration | Brain Penetration Ratio (Cb/Cp) |
|---|---|---|---|---|---|
| 1. | Wistar/Male | 1 | Water | Intravenous | 1.97 ± 0.24 |
|  |  | 3 | Water | Per Oral |  |
| 4. | Wistar/Male | 1 | Water | Intravenous | 2.17 ± 0.17 |
|  |  | 3 | Water | Per Oral |  |
| 5. | Wistar/Male | 1 | Water | Intravenous | 3.08 ± 0.45 |
|  |  | 3 | Water | Per Oral |  |
| 22. | Wistar/Male | 1 | Water | Intravenous | 2.10 ± 0.13 |
|  |  | 3 | Water | Per Oral |  |

Example 70

Object Recognition Task Model

The cognition enhancing properties of compounds of this invention were estimated by using this model.

Male Wister rats (230-280 grams) obtained from N. I. N. (National Institute of Nutrition, Hyderabad, India) was used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cms from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Ennaceur, A., Delacour, J., 1988, A new one-trial test for neurobiological studies of memory in rats—Behavioural data, Behav. Brain Res., 31, 47-59.

| Example Number | Dose mg/kg, p.o. | Exploration time mean ± S.E.M (sec) | | Inference |
|---|---|---|---|---|
| | | Familiar object | Novel object | |
| 1. | 3 mg/kg | 7.8 ± 1.80 | 23.95 ± 3.15 | Active |
| 4. | 10 mg/kg | 7.8 ± 1.36 | 20.32 ± 2.22 | Active |
| 5. | 3 mg/kg | 7.15 ± 0.91 | 11.44 ± 1.58 | Active |
| 28. | 0.3 mg/kg | 6.12 ± 1.22 | 11.44 ± 1.69 | Active |

Example 71

Morris Water Maze

The cognition-enhancing properties of compounds of this invention were estimated by using this model.

The water maze apparatus consisted of a circular pool (1.8 m diameter, 0.6 m high) constructed in black Perspex (TSE systems, Germany) filled with water (24±2° C.) and positioned underneath a wide-angled video camera to track animal. The 10 cm² perspex platform, lying 1 cm below the water surface, was placed in the centre of one of the four imaginary quadrants, which remained constant for all rats. The black Perspex used in the construction of the maze and platform offered no intramaze cues to guide escape behavior. By contrast, the training room offered several strong extramaze visual cues to aid the formation of the spatial map necessary for escape learning. An automated tracking system, [Videomot 2 (5.51), TSE systems, Germany] was employed. This program analyzes video images acquired via a digital camera and an image acquisition boards that determined path length, swim speed and the number of entries and duration of swim time spent in each quadrant of the water maze.

| Example Number | Reversal of Scopolamine Induced amnesia |
|---|---|
| 1. | ≤10 mg/kg, p.o. |
| 4. | ≤10 mg/kg, p.o. |
| 5. | ≤3 mg/kg, p.o. |
| 12. | ≥20 mg/kg, p.o. |
| 28. | ≥10 mg/kg, p.o. |

Example 72

Inhibition of Food Intake

The anti-obesity properties of compounds of this invention were estimated using this model The experiment consisted of 6 days. The rats were adapted to the 18 hours fasting and 6 hours feeding pattern. The animals were housed in a group of three in the cages provided with the fasting grills and was fasted for 18 hours. After 18 hours fasting the rats were separated and placed individually in the cage. Weighed amount of feed was provided to rats for 6 hours and the feed intake at 1 hour, 2 hours, 4 hours and 6 hours was measured Again the rats were regrouped and fasted for 18 hours. The above procedure was followed for 5 days. The average cumulative food intake by the rats on the last 3 days was calculated. Animals were randomized on the basis of their previous three days food intake. On the day of experiment the rats were orally treated test compounds or vehicle. After 60 minutes, the feed was provided to the rats and the food intake at 1 hour, 2 hours, 4 hours and 6 hours was measured. The food intake by the rats treated with test compound was compared with the vehicle treated group by using Unpaired Student's t test.

| Example Number | Inhibition of food intake |
| --- | --- |
| 4. | 20 mg/kg, p.o. |

We claim:

1. A compound of the general formula (I):

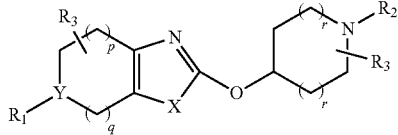

wherein,
$R_1$ is —C(O)—$R_4$, —S(O)$_2$—$R_4$,

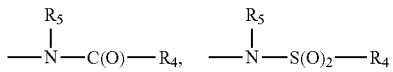

substituted or unsubstituted cycloalkyl, aryl or heteroaryl; wherein substituents, may be one or more and are independently selected from hydrogen, hydroxy, halogen, alkyl, alkoxy, haloalkyl or haloalkoxy;

$R_4$ is substituted or unsubstituted alkyl, cycloalkyl, cycloalkylalkyl, aryl, heteroaryl, heterocyclyl or heterocyclylalkyl; wherein substituents, may be one or more and are independently selected from hydrogen, hydroxy, halogen, alkyl, alkoxy, haloalkyl or haloalkoxy;

$R_5$ is hydrogen, alkyl or cycloalkyl;

at each occurrence, $R_3$ is independently selected from hydrogen, halo, alkyl or alkoxy;

$R_2$ is hydrogen, substituted or unsubstituted alkyl or cycloalkyl; wherein substituents, may be one or more and are independently selected from hydrogen, hydroxy, halogen, alkyl, alkoxy, haloalkyl or haloalkoxy;

X is S, N or O;

Y is C or N;

"p" is an integer ranging from 0 to 2;

"q" is an integer ranging from 0 to 2;

"r" is an integer ranging from 0 to 1; or a pharmaceutically acceptable salt thereof.

2. The compound as claimed in claim 1, wherein $R_2$ is alkyl or cylcoalkyl.

3. The compound as claimed in claim 1, wherein $R_3$ is hydrogen or alkyl.

4. The compound as claimed in claim 1, wherein $R_4$ is alkyl, cycloalkyl, cycloalkylalkyl, aryl, heteroaryl, heterocyclyl or heterocyclylalkyl.

5. The compound as claimed in claim 1, wherein $R_5$ is hydrogen.

6. The compound as claimed in claim 1, which is selected from the group consisting of:

1-[2-(1-Cyclobutyl-piperidin-4-yloxy)-6,7-dihydro-4H-thiazolo[5,4-c]pyridin-5-yl]-propan-1-one tartrate;

[2-(4-Cyclobutyl-cyclohexyloxy)-4,5,7,8-tetrahydro-thiazolo[5,4-d]azepin-6-yl]-cyclopropyl-methanone tartrate;

N-[2-(1-Cyclobutyl-piperidin-4-yloxy)-4,5,6,7-tetrahydro-benzothiazol-6-yl]-propionamide;

[2-(1-Cyclobutyl-piperidin-4-yloxy)-6,7-dihydro-4H-thiazolo[5,4-c]pyridin-5-yl]-cyclopropyl-methanone tartrate;

Cyclobutyl-[2-(1-cyclobutyl-piperidin-4-yloxy)-6,7-dihydro-4H-thiazolo[5,4-c]pyridin-5-yl]-methanone tartrate;

[2-(1-Cyclobutyl-piperidin-4-yloxy)-6,7-dihydro-4H-thiazolo[5,4-c]pyridin-5-yl]-(2-fluoro-phenyl)-methanone tartrate;

1-[2-(1-Cyclobutyl-piperidin-4-yloxy)-6,7-dihydro-4H-thiazolo[5,4-c]pyridin-5-yl]-3-methyl-butan-1-one tartrate;

Cyclobutyl-[2-(1-isopropyl-piperidin-4-yloxy)-6,7-dihydro-4H-thiazolo[5,4-c]pyridin-5-yl]-methanone;

Cyclopropyl-[2-(1-isopropyl-piperidin-4-yloxy)-6,7-dihydro-4H-thiazolo[5,4-c]pyridin-5-yl]-methanone tartrate;

Cyclopropyl-[2-(1-cyclopropyl-piperidin-4-yloxy)-6,7-dihydro-4H-thiazolo[5,4-c]pyridin-5-yl]-methanone tartrate;

Cyclobutyl-[2-(1-cyclopropyl-piperidin-4-yloxy)-6,7-dihydro-4H-thiazolo[5,4-c]pyridin-5-yl]-methanone tartrate;

1-[2-(1-Cyclobutyl-piperidin-4-yloxy)-6,7-dihydro-4H-thiazolo[5,4-c]pyridin-5-yl]-2-morpholin-4-yl-ethanone tartrate;

[4-(5-Cyclobutyl-,6,7-dihydro-4H-thiazolo[5,4-c]pyridin-2-yloxy)-piperidin-1-yl]-cyclopropyl-methanone tartrate;

[3-(5-Cyclobutyl-,6,7-dihydro-4H-thiazolo[5,4-c]pyridin-2-yloxy)-piperidin-1-yl]-cyclopropyl-methanone tartrate;

[2-(1-Cyclobutyl-piperidin-3-yloxy)-6,7-dihydro-4H-thiazolo[5,4-c]pyridin-5-yl]-cyclopropyl-methanone tartrate;

[2-(1-Cyclobutyl-piperidin-4-yloxy)-6,7-dihydro-4H-thiazolo[5,4-c]pyridin-5-yl]-pyridin-4-yl-methanone tartrate;

[2-(1-Cyclobutyl-piperidin-4-yloxy)-6,7-dihydro-4H-thiazolo[5,4-c]pyridin-5-yl]-(4-methoxy-phenyl)-methanone tartrate;

1-[2-(1-Cyclobutyl-piperidin-4-yloxy)-6,7-dihydro-4H-thiazolo[5,4-c]pyridin-5-yl]-2-piperidin-1-yl-ethanone tartrate;

1-[2-(1-Cyclobutyl-piperidin-4-yloxy)-6,7-dihydro-4H-thiazolo[5,4-c]pyridin-5-yl]-2-cyclopropyl-ethanone;

2-(1-Cyclobutyl-piperidin-4-yloxy)-5-(2-fluoro-benzenesulfonyl)-,6,7-dihydro-4H-thiazolo[5,4-c]pyridine tartrate;

2-(1-Cyclobutyl-piperidin-4-yloxy)-5-methanesulfonyl-, 6,7-dihydro-4H-thiazolo[5,4-c]pyridine;
1-[2-(1-Cyclobutyl-piperidin-4-yloxy)-6,7-dihydro-4H-thiazolo[5,4-c]pyridin-5-yl]-2-methyl-propan-1-one tartrate;
2-(1-Cyclobutyl-piperidin-4-yloxy)-5-(2-trifluoromethyl-pyridin-5-yl)-,6,7-dihydro-4H-thiazolo[5,4-c]pyridine;
Cyclopropyl-[2-(1-isobutyl-piperidin-4-yloxy)-6,7-dihydro-4H-thiazolo[5,4-c]pyridin-5-yl]-methanone tartrate;
[2-(1-Cyclobutyl-piperidin-4-yloxy)-6,7-dihydro-4H-thiazolo[5,4-c]pyridin-5-yl]-(2-trifluoromethyl-pyridin-5-yl)-methanone;
[2-(1-Cyclobutyl-piperidin-4-yloxy)-6,7-dihydro-4H-thiazolo[5,4-c]pyridin-5-yl]-pyridin-3-yl-methanone tartrate;
2-(1-Cyclobutyl-piperidin-4-yloxy)-5-pyridin-3-yl-,6,7-dihydro-4H-thiazolo[5,4-c]pyridine tartrate;
[2-(1-Cyclobutyl-piperidin-4-yloxy)-6,7-dihydro-4H-thiazolo[5,4-c]pyridin-5-yl]-(tetrahydro-pyran-4-yl)-methanone;
[2-(1-Cyclobutyl-piperidin-4-yloxy)-6,7-dihydro-4H-thiazolo[5,4-c]pyridin-5-yl]-morpholin-4-yl-methanone tartrate;
[2-(1-Cyclobutyl-piperidin-4-yloxy)-6,7-dihydro-4H-thiazolo[5,4-c]pyridin-5-yl]-piperidin-1-yl-methanone hydrochloride;
6-[2-(1-Cyclobutyl-piperidin-4-yloxy)-6,7-dihydro-4H-thiazolo[5,4-c]pyridin-5-yl]-nicotinamide;
[2-(1-Cyclobutyl-piperidin-4-yloxy)-6,7-dihydro-4H-thiazolo[5,4-c]pyridin-5-yl]-cyclopentyl-methanone tartrate;
[2-(1-Cyclobutyl-piperidin-4-yloxy)-6,7-dihydro-5H-thiazolo[5,4-b]pyridin-4-yl]-cyclopropyl-methanone tartrate;
Cyclopropyl-[2-(1-isopropyl-piperidin-4-yloxy)-4,5,7,8-tetrahydro-thiazolo[5,4-d]azepin-6-yl]-methanone tartrate;
[2-(1-Cyclobutyl-piperidin-4-yloxy)-6,7-dihydro-5H-thiazolo[5,4-b]pyridin-4-yl]-cyclopropyl-methanone;
1-[2-(1-Cyclobutyl-piperidin-4-yloxy)-6,7-dihydro-5H-thiazolo[5,4-b]pyridin-4-yl]-propan-1-one;
Cyclobutyl-[2-(1-cyclobutyl-piperidin-4-yloxy)-6,7-dihydro-5H-thiazolo[5,4-b]pyridin-4-yl]-methanone;
N-[2-(1-Cyclobutyl-piperidin-4-yloxy)-4,5,6,7-tetrahydro-benzothiazol-7-yl]-propionamide;
1-[2-(1-Cyclobutyl-piperidin-4-yloxy)-6,7-dihydro-4H-oxazolo[5,4-c]pyridin-5-yl]-propan-1-one;
1-[2-(1-Cyclobutyl-piperidin-4-yloxy)-4,6-dihydro-pyrrolo[4,3-d]oxazol-5-yl]-propan-1-one;
N-[2-(1-Cyclobutyl-piperidin-4-yloxy)-5,6-dihydro-4H-cyclopentaoxazol-5-yl]-propionamide;
N-[2-(1-Cyclobutyl-piperidin-4-yloxy)-5,6-dihydro-4H-cyclopentathiazol-5-yl]-propionamide;
1-[2-(1-Cyclobutyl-piperidin-4-yloxy)-4,6-dihydro-pyrrolo[4,3-d]thiazol-5-yl]-propan-1-one;
1-[2-(1-Cyclobutyl-piperidin-4-yloxy)-5,6-dihydro-pyrrolo[3,2-d]thiazol-4-yl]-propan-1-one;
N-[2-(1-Cyclobutyl-piperidin-4-yloxy)-5,6-dihydro-4H-cyclopentathiazol-6-yl]-propionamide;
N-[2-(1-Cyclobutyl-piperidin-4-yloxy)-5,6-dihydro-4H-cyclopentaoxazol-6-yl]-propionamide;
1-[2-(1-Cyclobutyl-piperidin-4-yloxy)-5,6-dihydro-pyrrolo[3,2-d]oxazol-4-yl]]-propan-1-one;
1-[2-(1-Cyclobutyl-piperidin-4-yloxy)-4,6-dihydro-pyrrolo[4,3-d]oxazol-5-yl]-propan-1-one;
N-[2-(1-Cyclobutyl-piperidin-4-yloxy)-5,6-dihydro-4H-cyclopentaoxazol-5-yl]-propionamide;
1-[2-(1-Cyclobutyl-piperidin-4-yloxy)-4,6,7,8-tetrahydro-thiazolo[5,4-c]azepin-5-yl]-propan-1-one;
1-[2-(1-Cyclobutyl-piperidin-4-yloxy)-4-methyl-6,7-dihydro-4H-thiazolo[5,4-c]pyridin-5-yl]-propan-1-one;
1-[2-(1-Cyclobutyl-piperidin-4-yloxy)-7-fluoro-6,7-dihydro-4H-thiazolo[5,4-c]pyridin-5-yl]-propan-1-one;
1-[2-(1-Cyclobutyl-piperidin-4-yloxy)-7-methyl-6,7-dihydro-4H-thiazolo[5,4-c]pyridin-5-yl]-propan-1-one;
1-[2-(1-Cyclobutyl-piperidin-4-yloxy)-6-methyl-6,7-dihydro-4H-thiazolo[5,4-c]pyridin-5-yl]-propan-1-one;
1-[2-(1-Cyclobutyl-3-methyl-piperidin-4-yloxy)-6,7-dihydro-4H-thiazolo[5,4-c]pyridin-5-yl]-propan-1-one;
1-[2-(1-Cyclobutyl-3-fluoro-piperidin-4-yloxy)-6,7-dihydro-4H-thiazolo[5,4-c]pyridin-5-yl]-propan-1-one;
1-Cyclobutyl-4-(5-propionyl-4,5,6,7-tetrahydro-thiazolo[5,4-c]pyridin-2-yloxy)-piperidine-3-carbonitrile;
1-[2-(1-Cyclobutyl-azepan-4-yloxy)-6,7-dihydro-4H-thiazolo[5,4-c]pyridin-5-yl]-propan-1-one;
1-[2-(1-Cyclobutyl-azepan-4-yloxy)-4,5,7,8-tetrahydro-thiazolo[5,4-d]azepin-6-yl]-propan-1-one;
1-[2-(1-Cyclobutyl-pyrrolidin-3-yloxy)-4,5,7,8-tetrahydro-thiazolo[5,4-d]azepin-6-yl]-propan-1-one;
1-[2-(1-Cyclobutyl-pyrrolidin-3-yloxy)-4,6-dihydro-pyrrolo[4,3-d]thiazol-5-yl]-propan-1-one;
1-[2-(1-Cyclobutyl-azepan-4-yloxy)-4,6-dihydro-pyrrolo[4,3-d]thiazol-5-yl]-propan-1-one;
1-{2-[1-(2-Hydroxy-ethyl)-piperidin-4-yloxy]-6,7-dihydro-4H-thiazolo[5,4-c]pyridin-5-yl}-propan-1-one;
1-[2-(1-Ethoxymethyl-piperidin-4-yloxy)-6,7-dihydro-4H-thiazolo[5,4-c]pyridin-5-yl]-propan-1-one;
1-{2-[1-(2,2,2-Trifluoro-ethyl)-piperidin-4-yloxy]-6,7-dihydro-4H-thiazolo [5,4-c]pyridin-5-yl}-propan-1-one;
1-[2-(1-Cyclobutyl-azetidin-3-yloxy)-6,7-dihydro-4H-thiazolo[5,4-c]pyridin-5-yl]-propan-1-one; and their pharmaceutically acceptable salts.

7. A pharmaceutical composition comprising a compound according to claim 1 and pharmaceutically acceptable excipient.

8. The pharmaceutical composition as claimed in claim 7, for the treatment of clinical conditions such as cognitive disorders, sleep disorders, obesity and pain.

9. A process for the preparation of a compound of formula (I) as claimed in claim 1, which comprises:

(a) coupling the compound of formula (1) with compound of formula (2)

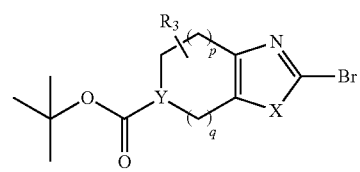

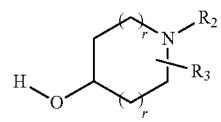

to form a compound of formula (3),

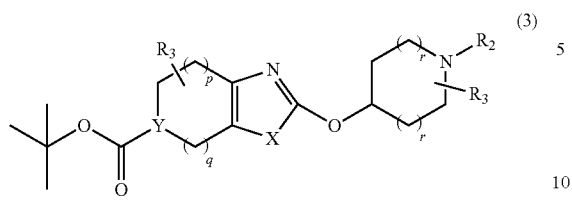

(b) deprotecting the compound of formula (3) to form compound of formula (4),

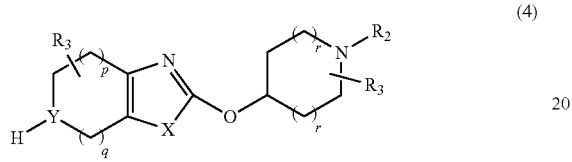

(c) coupling the compound of formula (4) with compound of formula (5)

to form a compound of formula (I), wherein all substitutions are as defined in claim 1, (d) optionally converting the compound of formula (I) to their pharmaceutically acceptable salts.

10. A process for the preparation of a compound of formula (I) as claimed in claim 1, which comprises:

(a) coupling the compound of formula (6) with compound of formula (5)

to form compound of formula (7),

(b) bromination of compound of formula (7) to form compound of formula (8),

(c) cyclization of compound of formula (8) to form compound of formula (9),

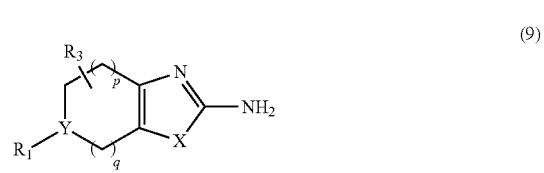

(d) diazotization of compound of formula (9) to form compound of formula (10),

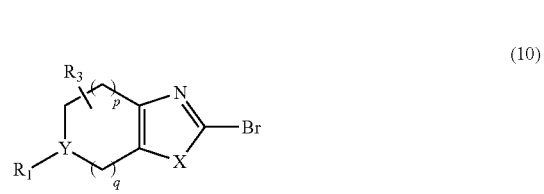

(e) coupling the compound of formula (10) with compound of formula (2)

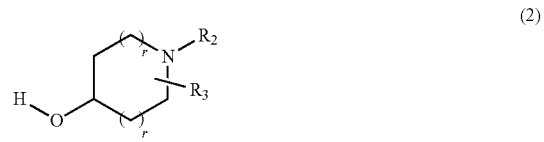

to form compound of formula (I), wherein all substitutions are as defined in claim 1, (f) optionally converting the compound of formula (I) to their pharmaceutically acceptable salts.

11. A process for the preparation of a compound of formula (I) as claimed in claim 1, which comprises:

(a) coupling the compound of formula (11) with compound of formula (5),

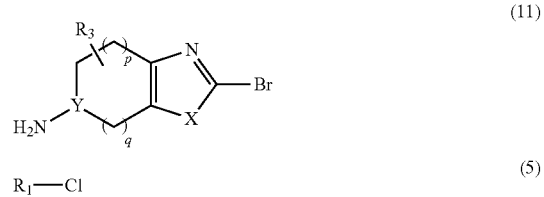

to form a compound of formula (12),

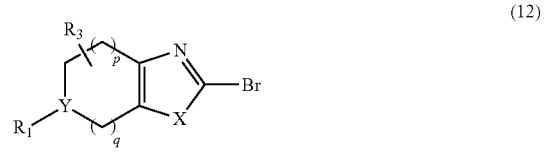

(b) coupling the compound of formula (12) with compound of formula (2)

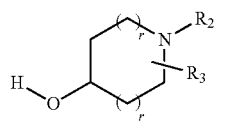 (2)

to form a compound of formula (I), wherein all substitutions are as defined in claim 1,
(c) optionally converting the compound of formula (I) to their pharmaceutically acceptable salts.

12. A method of treating cognitive disorders, sleep disorders, obesity or pain, comprising administering to a patient in need thereof an effective amount of a compound or pharmaceutically acceptable salt thereof according to claim 1.

\* \* \* \* \*